(12) United States Patent
Sugiyama et al.

(10) Patent No.: US 9,423,343 B2
(45) Date of Patent: Aug. 23, 2016

(54) MEMBRANE POTENTIAL CHANGE DETECTION DEVICE AND MEMBRANE POTENTIAL CHANGE DETECTION METHOD

(75) Inventors: Norikazu Sugiyama, Hamamatsu (JP); Takuji Kataoka, Hamamatsu (JP); Takahiro Ikeda, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 322 days.

(21) Appl. No.: 13/642,066

(22) PCT Filed: Apr. 13, 2011

(86) PCT No.: PCT/JP2011/059186
§ 371 (c)(1),
(2), (4) Date: Dec. 21, 2012

(87) PCT Pub. No.: WO2011/132584
PCT Pub. Date: Oct. 27, 2011

(65) Prior Publication Data
US 2013/0088719 A1 Apr. 11, 2013

(30) Foreign Application Priority Data
Apr. 23, 2010 (JP) ................................. 2010-100284

(51) Int. Cl.
*G01N 21/45* (2006.01)
*C12Q 1/02* (2006.01)
*G01N 21/25* (2006.01)

(52) U.S. Cl.
CPC ................ *G01N 21/45* (2013.01); *C12Q 1/02* (2013.01); *G01N 21/253* (2013.01)

(58) Field of Classification Search
USPC ....................................................... 356/450
See application file for complete search history.

(56) References Cited

U.S. PATENT DOCUMENTS

2007/0035819 A1* 2/2007 Bahatt ................ G01N 21/0332
359/366
2008/0262741 A1* 10/2008 Harris et al. .................... 702/19
2009/0128825 A1* 5/2009 Akcakir ........................ 356/457

FOREIGN PATENT DOCUMENTS

| JP | 2008-506098 | 2/2008 |
|---|---|---|
| JP | 2009-63375 | 3/2009 |
| JP | 2009-148224 | 7/2009 |

OTHER PUBLICATIONS

Raimund Gleixner et al., "The Extracellular Electrical Resistivity in Cell Adhesion," Biophysical Journal, Apr. 2006, pp. 2600-2611, vol. 90.

(Continued)

*Primary Examiner* — Tarifur Chowdhury
*Assistant Examiner* — Omar Nixon
(74) *Attorney, Agent, or Firm* — Drinker Biddle & Reath LLP

(57) ABSTRACT

A membrane potential change detection device is provided with a reflection interference measurement light source, a holder which holds a transparent member on which cells are mounted, a reflection interference detection camera which images light emitted from the reflection interference measurement light source and reflected from the cells through the transparent member, to generate a reflection interference image, and an analysis unit which calculates a parameter dI about adhesion between the cells and the transparent member from the reflection interference image and detects a change of membrane potential of the cells on the basis of a change of the parameter dI.

13 Claims, 24 Drawing Sheets

(56) References Cited

OTHER PUBLICATIONS

Jesús E. González et al., "Improved indicators of cell membrane potential that use fluorescence resonance energy transfer," Chemistry & Biology, 1997, pp. 269-277, vol. 4, No. 4.

Christopher Fang-Yen et al., "Noncontact measurement of nerve displacement during action potential with a dual-beam low-coherence interferometer," Optics Letter, Sep. 1, 2004, pp. 2028-2030, vol. 29, No. 17.

Toyohiko Yamauchi et al., "Low-coherent quantitative phase microscope for nanometer-scale measurement of living cells morphology," Optics Express, Aug. 4, 2008, pp. 12227-12238, vol. 16, No. 16.

Miloš Todorović et al., "Determination of local polarization properties of biological samples in the presence of diattenuation by use of Mueller optical coherence tomography," Optics Letter, Oct. 15, 2004, pp. 2402-2404, vol. 29, No. 20.

* cited by examiner

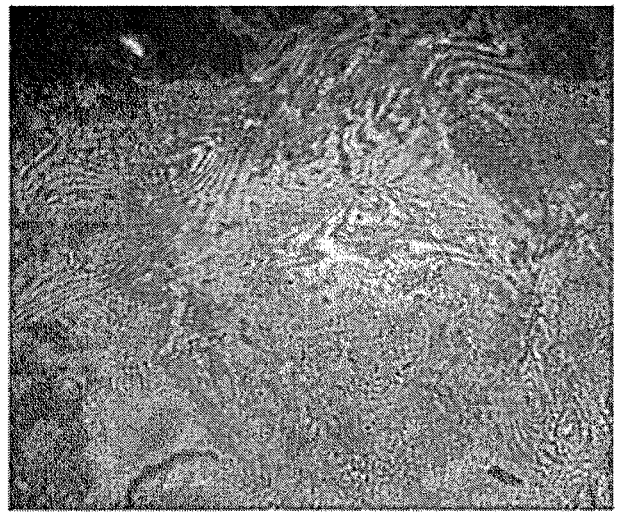
BOTTOM OF VESSEL WITH ANTIREFLECTION COAT
(B)
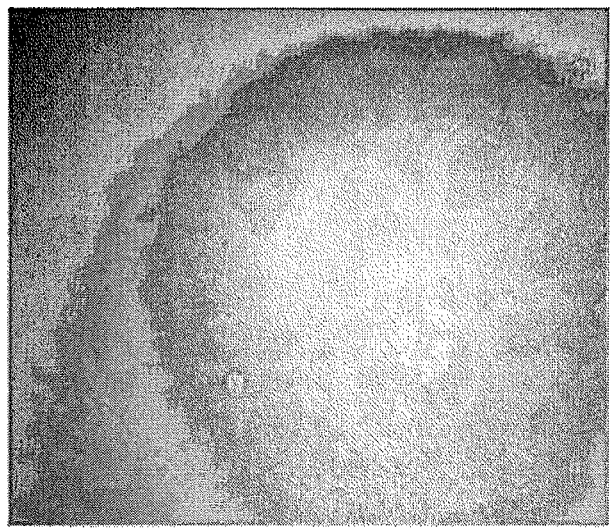
UNTREATED
(A)
Fig.5

Fig.8
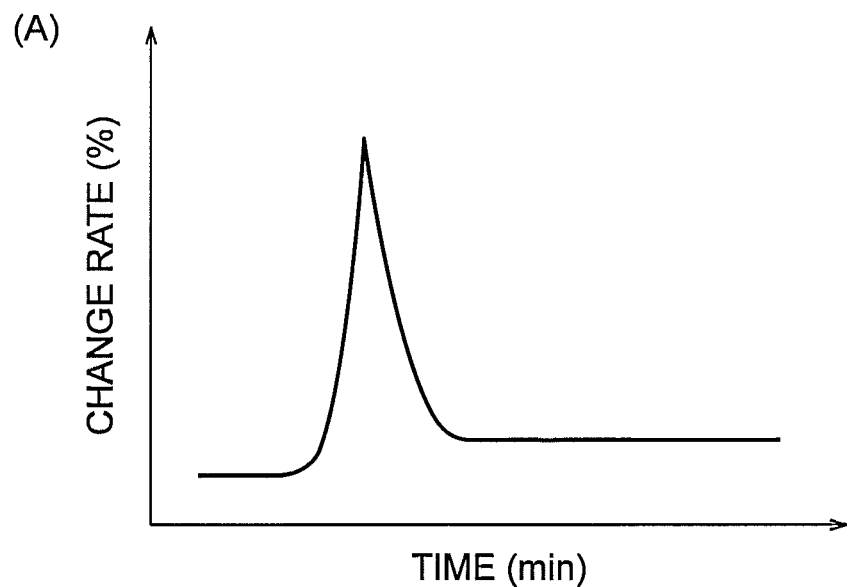
(A)
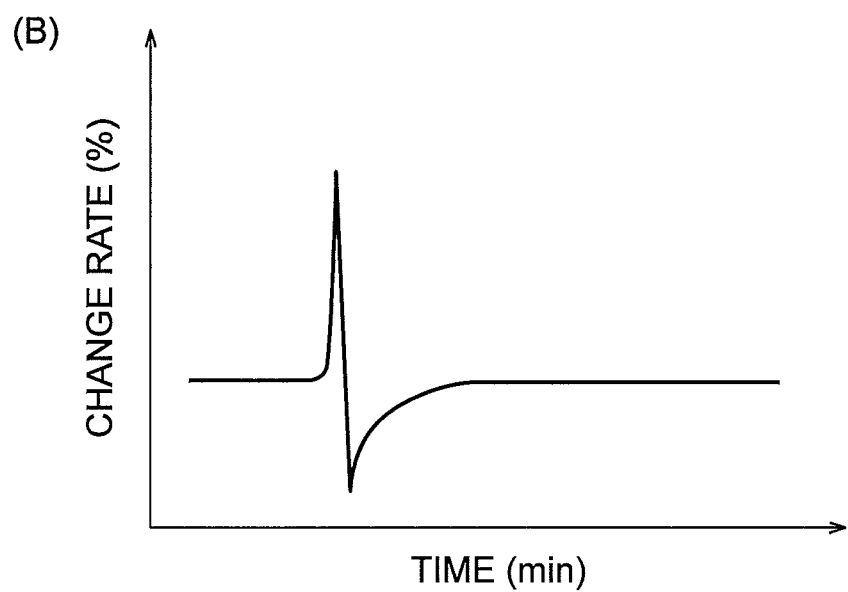
(B)

MEMBRANE POTENTIAL CHANGE DETECTION DEVICE AND MEMBRANE POTENTIAL CHANGE DETECTION METHOD

TECHNICAL FIELD

The present invention relates to a membrane potential change detection device and a membrane potential change detection method.

BACKGROUND ART

Development of investigational agents targeting ion channels of cells has been increasing its importance in development of new drugs. The conventional assays using living cells have been conducted using measurement of membrane potential with a patch-clamp electrode, optical measurement of membrane potential using a voltage sensitive dye, and so on. For example, Non Patent Literature 1 discloses the technology to dye a cell with a fluorescent pigment and obtain a distance between the cell mounted on a substrate, and the substrate (degree of adhesion of the cell), using a fluorescence interference contrast microscope image, and the technology to dye a cell with a voltage sensitive dye and optically obtain a change of membrane potential of the cell. Furthermore, Non Patent Literature 2 discloses the technology to dye (or color) a cell with a FRET dye and calculate a change of cell membrane potential using the FRET phenomenon.

CITATION LIST

Non Patent Literatures

Non Patent Literature 1: Raimund Gleixner and Peter Fromherz, "The Extracellular Electrical Resistivity in Cell Adhesion," Biophysical Journal, Volume 90, 2600-2611 (2006)

Non Patent Literature 2: Jesus E Gonzalez and Roger YTsien, "Improved Indicators of cell membrane potential that use fluorescence resonance energy transfer," Chemistry & Biology, 1997, Vol. 4, Page. 269-277

SUMMARY OF INVENTION

Technical Problem

The fluorescent pigment as a labeling agent for measurement of the change of cell membrane potential needs to be incorporated into the cell. Furthermore, the aforementioned measurement requires illumination with strong excitation light, which affects the state of living cells. For measurement with living cells being kept in a normal condition, an optimum condition of dye concentration or irradiation intensity of excitation light needs to be determined through trial and error. If human cells on the basis of stem cells are increasingly used as an object of evaluation of drug efficacy in the future, measurements with labeling will become harder and harder because there are many cells susceptible to damage among such cells. Therefore, there are desires for label-free technology to non-invasively measure the membrane potential without labeling as much as possible and with cells being kept untouched as much as possible from a cultivated state.

The present invention has been accomplished in view of the above circumstances and it is an object of the present invention to provide a membrane potential change detection device and a membrane potential change detection method capable of detecting a change of membrane potential of a cell by a non-invasive method without labeling.

Solution to Problem

In order to solve the above problem, a membrane potential change detection device of the present invention is one comprising: a reflection interference measurement light source; holding means which holds a transparent member on which a cell is mounted; reflection interference imaging means which images light emitted from the reflection interference measurement light source and reflected from the cell through the transparent member, to generate a reflection interference image; and analysis means which calculates a parameter about adhesion between the cell and the transparent member from the reflection interference image and detects a change of membrane potential of the cell on the basis of a change of the parameter.

A membrane potential change detection method of the present invention is one comprising: a reflection interference imaging step wherein reflection interference imaging means images light emitted from a reflection interference measurement light source and reflected from a cell through a transparent member on which the cell is mounted, to generate a reflection interference image; and an analysis step wherein analysis means calculates a parameter about adhesion between the cell and the transparent member from the reflection interference image and detects a change of membrane potential of the cell on the basis of a change of the parameter.

According to this invention, the device and method comprise the reflection interference measurement light source, the holding means, the reflection interference imaging means, and the analysis means, whereby the parameter about adhesion between the cell and the transparent member is calculated on the basis of the reflected light from the cell and the change of membrane potential of the cell is detected on the basis of the change of the parameter. The inventors discovered that there was a correlation between the adhesion degree between the cell and the transparent member on which the cell is mounted, and the change of membrane potential of the cell. The present invention is characterized by using such discovered correlation to define the change of cell membrane potential as the change of adhesion distance (adhesion degree) between the cell and the transparent member. Since the parameter about adhesion between the cell and the transparent member based on the adhesion distance is obtained by a non-invasive method, the change of membrane potential of the cell can be non-invasively detected without labeling.

In the present invention, the analysis means may detect the change of membrane potential of the cell, based on such a correlation that when depolarized, the cell departs from the transparent member and when hyperpolarized, the cell approaches the transparent member. According to this invention, the change of membrane potential of the cell with the cell becoming depolarized and hyperpolarized can be detected based on the aforementioned correlation discovered by the inventors.

In the present invention, the device may further comprise an objective lens which condenses the light emitted from the reflection interference measurement light source and reflected from the cell, and the objective lens and the transparent member may be arranged with an air layer in between. According to this invention, operability of the objective lens improves and therefore it becomes easier to perform the imaging while scanning the entire area of the transparent member on which the cell is mounted. This increases the throughput in detection of the change of cell membrane potential.

In the present invention, an antireflection coat may be laid on a surface of the transparent member opposite to a mount surface thereof. According to this invention, even if the objective lens used is one of a dry type, the reflection interference image of a cell adhesion face can be obtained with high contrast.

In the present invention, the device may further comprise a slit of a ring shape located at a position conjugate with an aperture stop on the reflection interference measurement light source side of the objective lens. According to this invention, the illumination light from the reflection interference measurement light source passes through the slit opening in the ring shape, the illumination light passes through the periphery without passing through the center of the objective lens, to illuminate the cell, and thus the cell is illuminated using only angled light with high NA; therefore, it is feasible to reduce influence of reflected light from a solution above the cell. Use of the ring-shape slit can also decrease background light due to reflection inside the objective lens.

In the present invention the device may further comprise: a quantitative phase measurement light source; and quantitative phase imaging means which images light emitted from the quantitative phase measurement light source and transmitted through the cell, to generate a quantitative phase image. According to this invention, the device comprises the quantitative phase measurement light source and the quantitative phase imaging means, whereby it acquires information such as the optical thickness, volume, and area of each individual cell. With the use of the information such as the optical thickness, volume, and area of each individual cell acquired from the quantitative phase imaging means, it becomes feasible to increase variations of the parameter about adhesion between the cell and the transparent member.

The membrane potential change detection device of the present invention may be configured as follows: it further comprises image alignment means which matches a spatial position of the reflection interference image with a spatial position of the quantitative phase image to implement alignment between the two images; contour extraction means which extracts a contour of the cell, based on the quantitative phase image; and contour application means which applies the contour extracted by the contour extraction means, to the reflection interference image to generate a reflection interference image after contour application; the analysis means calculates a parameter of each cell about adhesion between the cell and the transparent member, based on the reflection interference image after contour application, and detects a change of membrane potential of each cell on the basis of a change of the parameter.

Another membrane potential change detection method of the present invention may be one comprising: a reflection interference imaging step wherein reflection interference imaging means images light emitted from a reflection interference measurement light source and reflected from a cell through a transparent member on which the cell is mounted, to generate a reflection interference image; a quantitative phase imaging step wherein quantitative phase imaging means images light emitted from a quantitative phase measurement light source and transmitted through the cell, to generate a quantitative phase image; an image alignment step wherein image alignment means matches a spatial position of the reflection interference image with a spatial position of the quantitative phase image to implement alignment between the two images; a contour extraction step wherein contour extraction means extracts a contour of the cell, based on the quantitative phase image; a contour application step wherein contour application means applies the contour extracted by the contour extraction means, to the reflection interference image to generate a reflection interference image after contour application; and an analysis step wherein analysis means calculates a parameter of each cell about adhesion between the cell and the transparent member, based on the reflection interference image after contour application, and detects a change of membrane potential of each cell on the basis of a change of the parameter.

According to these aspects of the invention, the device and method comprise the image alignment means, the contour extraction means, and the contour application means, whereby the contour of the cell is extracted based on the quantitative phase image and the contour is superimposed on the reflection interference image. This enables such operation that when a plurality of cells are included in the images acquired by the reflection interference imaging means and the quantitative phase imaging means, the change of membrane potential is detected for each of the individual cells.

In the present invention, the device may be configured as follows: it further comprises: reflection interference light quantity adjustment means which adjusts a light quantity of the light emitted from the reflection interference measurement light source; a quantitative phase measurement light source; and quantitative phase light quantity adjustment means which adjusts a light quantity of light emitted from the quantitative phase measurement light source, wherein the reflection interference imaging means images the reflected light from the cell, of the light emitted from the reflection interference measurement light source, to generate the reflection interference image, and images transmitted light through the cell, of the light emitted from the quantitative phase measurement light source, to generate a quantitative phase image; during generation of the reflection interference image, the quantitative phase light quantity adjustment means blocks the light from the quantitative phase measurement light source and the reflection interference imaging means images the reflected light; during generation of the quantitative phase image, the reflection interference light quantity adjustment means blocks the light from the reflection interference measurement light source and the reflection interference imaging means images the transmitted light. According to this invention, the device comprises the quantitative phase measurement light source and the quantitative phase imaging means, whereby it acquires the information such as the optical thickness, volume, and area of each individual cell. With the use of the information such as the optical thickness, volume, and area of each individual cell acquired from the quantitative phase imaging means, it becomes feasible to increase variations of the parameter about adhesion between the cell and the transparent member.

In the membrane potential change detection device of the present invention, the reflection interference light quantity adjustment means may be a shutter which adjusts the light quantity of the light emitted from the reflection interference measurement light source, and the quantitative phase light quantity adjustment means may be a shutter which adjusts the light quantity of the light emitted from the quantitative phase measurement light source. According to this invention, there is provided the specific means for adjustment of the light quantity of light.

In the membrane potential change detection device of the present invention, the reflection interference light quantity adjustment means may control switching of on/off of the reflection interference measurement light source to adjust the light quantity of the light emitted from the reflection interference measurement light source, and the quantitative phase light quantity adjustment means may control switching of on/off of the quantitative phase measurement light source to adjust the light quantity of the light emitted from the quantitative phase measurement light source. According to this invention, there is provided the specific method for adjustment of the light quantity of light. This method is useful, particularly, to cases where the light source is a semiconductor light source such as an LED (light emitting diode), an LD (laser diode), or an SLD (super luminescent diode).

The membrane potential change detection device of the present invention may be configured as follows: it further comprises contour extraction means which extracts a contour of the cell, based on the quantitative phase image; and contour application means which applies the contour extracted by the contour extraction means, to the reflection interference image to generate a reflection interference image after contour application; the analysis means calculates a parameter of each cell about adhesion between the cell and the transparent member, based on the reflection interference image after contour application, and detects a change of membrane potential of each cell on the basis of a change of the parameter.

Another membrane potential change detection method of the present invention may be one comprising: an imaging step wherein imaging means images reflected light from a cell, of light emitted from a reflection interference measurement light source, to generate a reflection interference image, and images transmitted light through the cell, of light emitted from a quantitative phase measurement light source, to generate a quantitative phase image; a contour extraction step wherein contour extraction means extracts a contour of the cell, based on the quantitative phase image; a contour application step wherein contour application means applies the contour extracted by the contour extraction means, to the reflection interference image to generate a reflection interference image after contour application; and an analysis step wherein analysis means calculates a parameter of each cell about adhesion between the cell and the transparent member, based on the reflection interference image after contour application, and detects a change of membrane potential of each cell on the basis of a change of the parameter, wherein during generation of the reflection interference image, quantitative phase light quantity adjustment means blocks the light from the quantitative phase measurement light source and the imaging means images the reflected light, and wherein during generation of the quantitative phase image, reflection interference light quantity adjustment means blocks the light from the reflection interference measurement light source and the imaging means images the transmitted light.

According to these aspects of the invention, the device and method comprise the image alignment means, the contour extraction means, and the contour application means, whereby the contour of the cell is extracted based on the quantitative phase image and the contour is superimposed on the reflection interference image. This enables such operation that when there are a plurality of cells included in the images acquired by the reflection interference imaging means and the quantitative phase imaging means, the change of membrane potential can be detected for each of the individual cells.

Advantageous Effect of Invention

The membrane potential change detection device and the membrane potential change detection method of the present invention enable the detection of the change of cell membrane potential by the non-invasive method without labeling.

BRIEF DESCRIPTION OF DRAWINGS

FIG. 5 is a drawing for illustrating an effect by an antireflection coat.

FIG. 8 is a drawing showing an example of temporal change of change rate.

DESCRIPTION OF EMBODIMENTS

The preferred embodiments of the membrane potential change detection device and the membrane potential change detection method according to the present invention will be described below in detail with reference to the accompanying drawings. In the description of the drawings the same elements will be denoted by the same reference signs, without redundant description.

The first embodiment will illustrate a device that detects a change of cell membrane potential by making use of a reflection interference image obtained from reflection interference measurement. The second embodiment and the third embodiment will illustrate methods for performing quantitative phase measurement simultaneously with reflection interference measurement to acquire a reflection interference image and a quantitative phase image, and detecting a change of cell membrane potential by making use of these two images.

First Embodiment

Overall Configuration of Membrane Potential Change Detection Device 1

Figure 1:
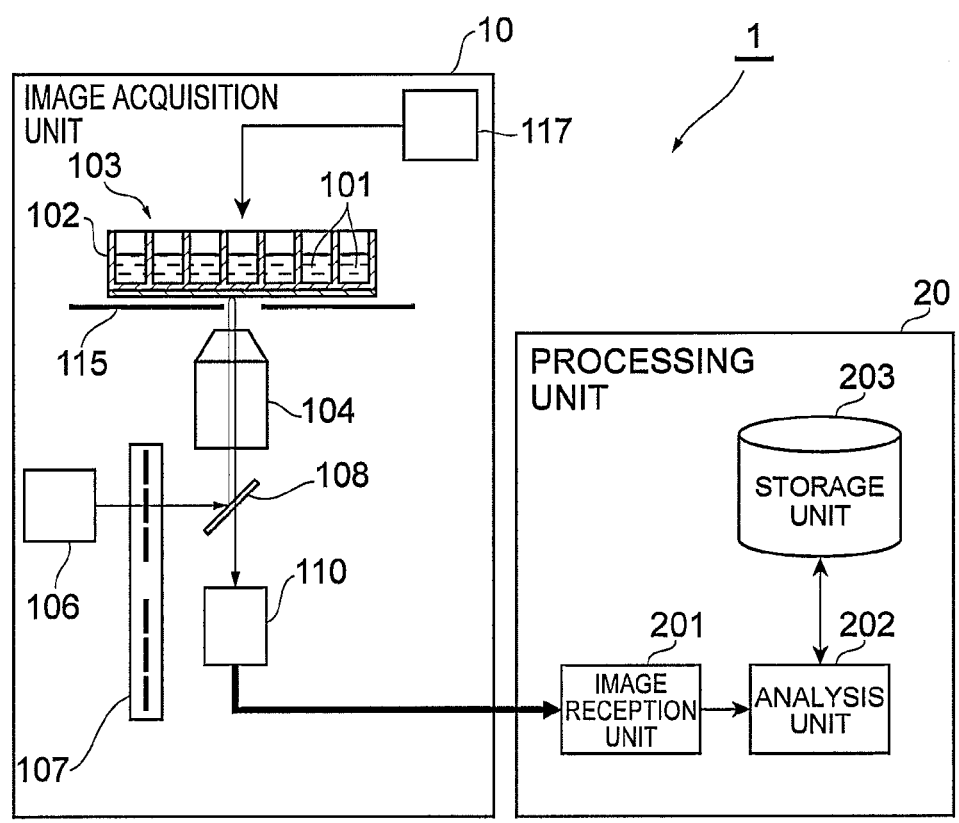
FIG. 1 is a schematic diagram showing an overall configuration of a membrane potential change detection device according to the first embodiment.

First, an overall configuration of a membrane potential change detection device 1 according to an embodiment of the present invention will be described with reference to FIG. 1. FIG. 1 is a schematic diagram showing the overall configuration of the membrane potential change detection device 1. As shown in FIG. 1, the membrane potential change detection device 1 is composed of an image acquisition unit 10 and a processing unit 20.

The image acquisition unit 10 is provided with a holder 103 (corresponding to "holding means" in the scope of claims), an objective lens 104, a reflection interference measurement light source 106, a slit 107 of a ring shape, a half mirror 108, a reflection interference detection camera 110 (corresponding to "reflection interference imaging means" in the scope of claims), an XY stage 115, and a dispenser 117. The processing unit 20 is provided with an image reception unit 201, an analysis unit 202 (corresponding to "analysis means" in the scope of claims), and a storage unit 203.

The holder 103 stationarily keeps (or holds) a vessel 102 which is formed of a transparent member 102a and in which cells 101 are housed (or mounted). The objective lens 104 condenses light emitted from the reflection interference measurement light source 106 and reflected from the cells 101. The objective lens 104 and the transparent member 102a are arranged with an air layer in between. The reflection interference measurement light source 106 emits illumination light. The ring-shape slit 107 realizes annular illumination. The half mirror 108 reflects or transmits incident light at a predetermined ratio. The reflection interference detection camera 110 images light emitted from the reflection interference measurement light source 106 and reflected from the cells 101 through the transparent member 102a, to generate a reflection interference image. The XY stage 115 implements switching of measurement regions. The dispenser 117 dispenses a chemical solution to the cells 101. The image reception unit 201 is a part that receives the reflection interference image output from the reflection interference detection camera 110. The analysis unit 202 is a part that calculates a parameter about adhesion between the cells and the transparent member from the reflection interference image and detects a change of cell membrane potential on the basis of the parameter. In the present embodiment, the analysis unit 202 detects the change of membrane potential of the cells 101, based on such a correlation that the cells 101 depart from the transparent member 102a when depolarized and the cells 101 approach the transparent member 102a when hyperpolarized. The storage unit 203 is a part that stores the parameter calculated by the analysis unit 202 and the image output from the reflection interference detection camera 110.

Figure 2:
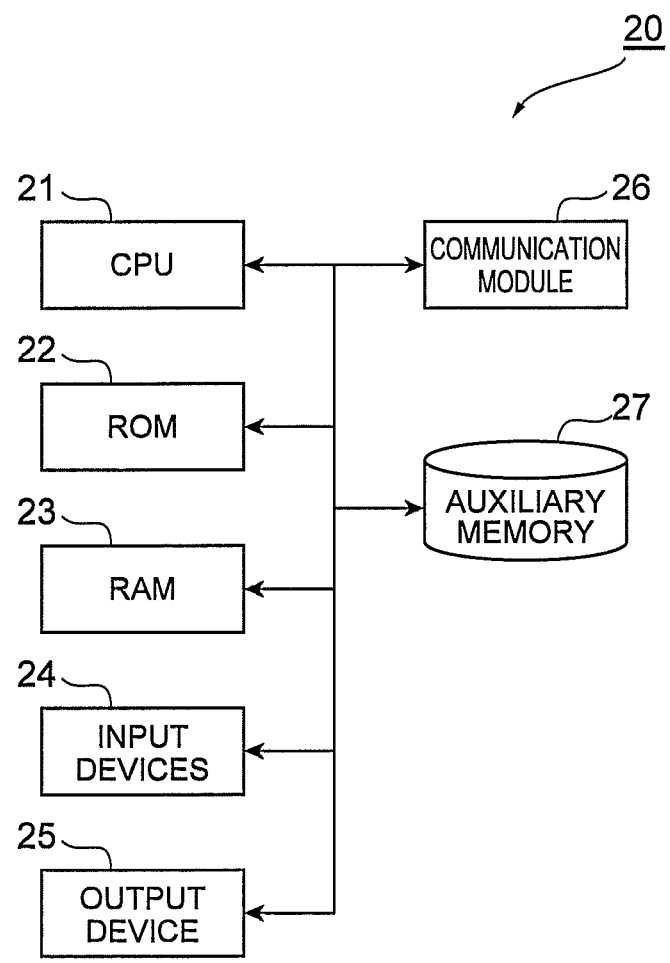
FIG. 2 is a hardware configuration diagram of a processing unit according to the first embodiment.

FIG. 2 is a hardware configuration diagram of the processing unit 20 having the functional constituent elements as described above. As shown in FIG. 2, the processing unit 20 is constructed, physically, as an ordinary computer system including a CPU 21, main memories such as ROM 22 and RAM 23, input devices 24 such as a keyboard and a mouse, an output device 25 such as a display, a communication module 26 such as a network card for transmission and reception of data to and from the image acquisition unit 10, and an auxiliary memory 27 such as a hard disk. Each of the functions of the processing unit 20 is substantialized in such a manner that predetermined computer software is retrieved onto the hardware such as the CPU 21, ROM 22, and RAM 23 to make the input devices 24, output device 25, and communication module 26 operate under control of the CPU 21 and data is read out and written into the main memories 22, 23 and the auxiliary memory 27.

(Detailed Description of Membrane Potential Change Detection Device 1)

(Description of Image Acquisition Unit 10)

The description will be given referring again to FIG. 1. The holder 103 is preferably maintained at a temperature suitable for a state of cells 101, in order to maintain the state of cells 101 under measurement. When the measurement of cells 101 is carried out over a long period, the holder 103 is preferably maintained in an environment at controlled temperature, humidity, carbon dioxide concentration, etc. suitable for development or state maintenance of the cells 101.

Figure 3:
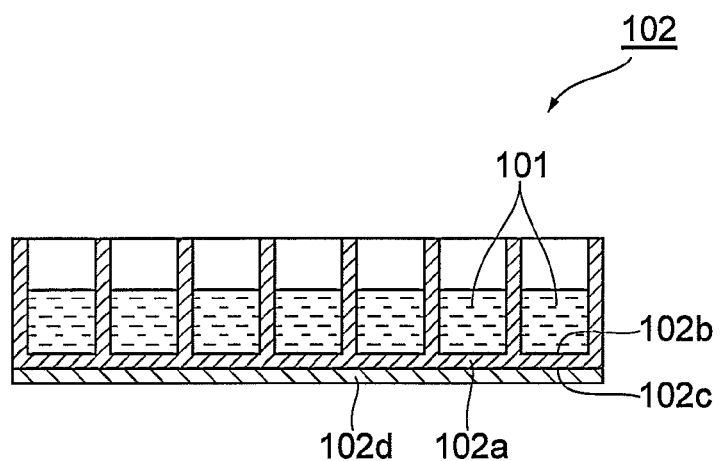
FIG. 3 is a sectional view showing a configuration of a vessel.

FIG. 3 is a sectional view showing a configuration of the vessel 102. The vessel 102 held by the holder 103 is configured so that the part on which the cells 101 are mounted is formed of the transparent member 102a. The vessel 102 can be, for example, a dish or a microplate as an example. A mount surface 102b of cells 101 in the vessel 102 is charged and in the present embodiment it is positively charged.

The vessel 102 is provided with an antireflection coat 102d laid on the opposite side (or on the objective lens 104 side of an observation region of the vessel) 102c to the mount surface 102b of the cells 101. This antireflection coat 102d exerts a pronounced effect on acquisition of the reflection interference image. For measuring the cells 101 as many as possible, it is preferable to use a low-magnification objective lens. However, the low-magnification objective lens has a low numerical aperture (NA: Numerical Aperture), which is usually not of an oil immersion or water immersion type, but is generally an objective lens of a dry type. However, when the reflection interference image is taken using the objective lens of the dry type, the illumination light emerging from the objective lens is significantly reflected on the bottom surface of the vessel housing the cells. This is because the refractive index difference between air and glass of the bottom surface of the vessel is large. For this reason, the background light increases considerably and it becomes almost difficult to observe the reflection interference image of the adhesion faces of cells. This is the reason why the objective lens of the oil immersion or water immersion type has been used heretofore for reflection interference observation.

Figure 4:
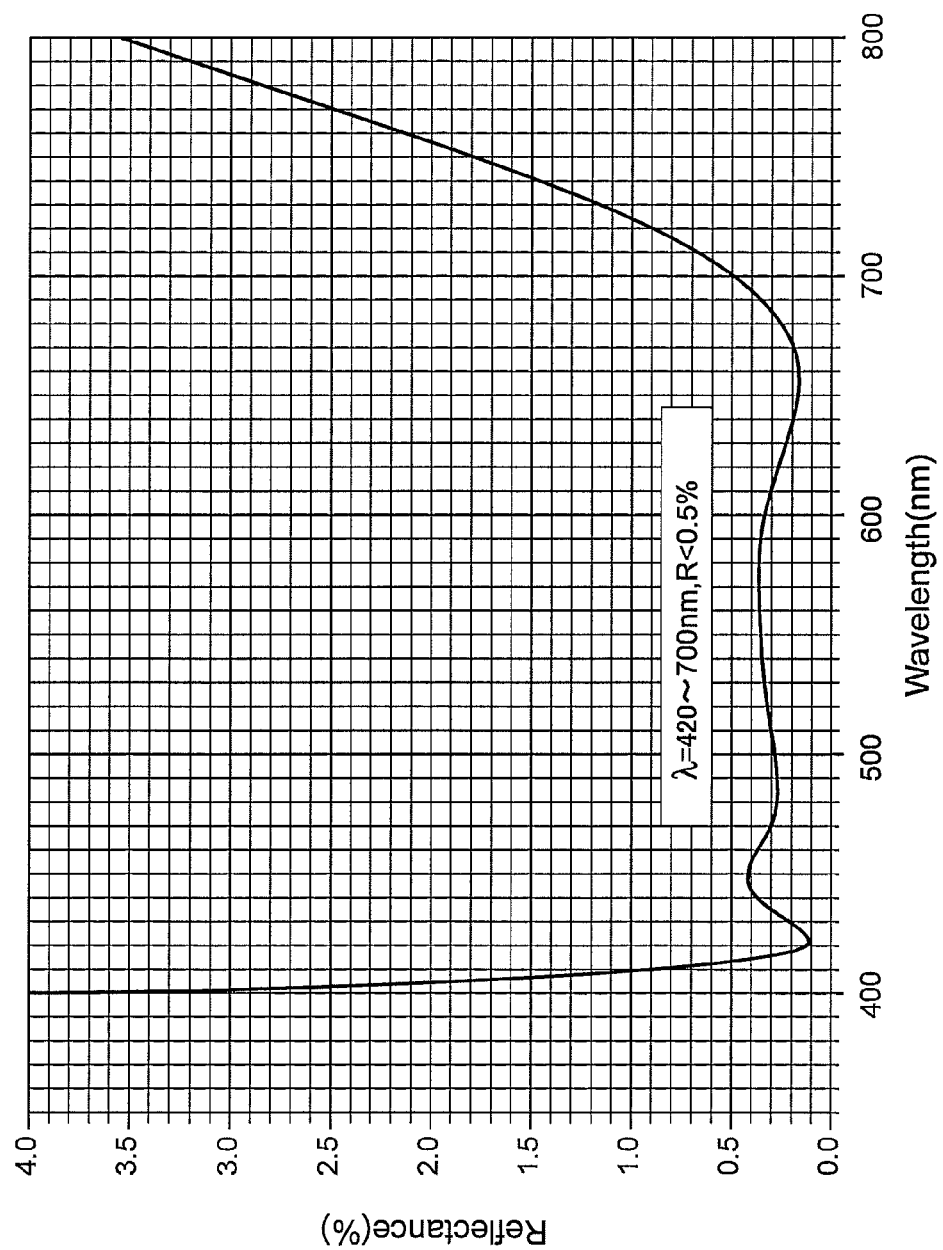
FIG. 4 is a drawing for illustrating an effect by an antireflection coat.

Therefore, the vessel 102 in the present embodiment is provided with the antireflection coat 102d on the side 102c opposite to the mount surface 102b of the cells 101 in the vessel 102 housing the cells 101, thereby enabling the acquisition of the reflection interference image with the use of the objective lens of the dry type. As shown in FIG. 4, the illumination light from the objective lens without the antireflection coat 102d is reflected approximately 4% at the interface between air and glass, whereas when the bottom surface of glass is subjected to an antireflection coat treatment to control the reflectance R to about 0.5% in the wavelength range of the illumination light (420 nm to 720 nm), the background light can be reduced to one eighth or below. For this reason, the present embodiment allows the reflection interference image of cell adhesion faces to be obtained with high contrast, even with the use of the objective lens of the dry type.

FIG. 5 shows the reflection interference image taken with the use of the dry objective lens in the configuration where the antireflection coat 102d is laid on the bottom surface 102c of the vessel 102. Without the antireflection coat 102d, as shown in (A) of FIG. 5, the reflection interference image comes to have extremely low contrast because of the significant reflection from the bottom surface 102c of the vessel 102. In contrast to it, when the vessel used is the vessel 102 with the antireflection coat 102d on the bottom surface 102c, as shown in (B) of FIG. 5, high contrast can be achieved even with the objective lens of the dry type.

Referring back to FIG. 1, the objective lens 104 is preferably one having a low magnification of 10 times or 20 times and a larger numerical aperture, in order to view as many cells as possible in the field as described above. The objective lens 104 is preferably not one of the water immersion or oil immersion type, but one of the dry type as described above. Since the present embodiment employs the objective lens of the dry type as described above, the operability of the objective lens 104 is improved, whereby imaging can be performed while scanning the entire area of the vessel 102. This can increase the throughput in detection of the change of membrane potential of the cells 101. The objective lens 104 is equipped with an unillustrated focus mechanism and therefore autofocus can be executed based on the image acquired by the reflection interference detection camera 110 described below.

The reflection interference measurement light source 106 is preferably a light source with radiation sensitivity over a wide wavelength band such as a halogen lamp or a xenon lamp. The illumination light having been used heretofore is that obtained using a band-pass filter to limit the wavelength band to some extent in order to achieve some contrast. However, the band-passed illumination light has high coherency and it is often the case therewith that interference fringes are also imaged due to reflection from an interface between an upper cell membrane of a cell and a culture solution unrelated to an adhesion face of cell. The present embodiment employs low-coherent light with a wide wavelength band and with low coherency. The use of the illumination light with the wide wavelength band can narrow the distance of occurrence of interference and enables extraction of the reflection interference image as being limited to the adhesion faces of the cells to the substrate. When the light source used is one with radiation sensitivity over a wide wavelength band such as a halogen lamp or a xenon lamp, light in the near infrared region from 700 nm to 2500 nm can be used as illumination light, which can reduce toxicity to the cells 101. The reflection interference measurement light source 106 to be used may be a light source such as an LED (light emitting diode), a semiconductor laser (laser diode), or an SLD (super luminescent diode).

Figure 6:
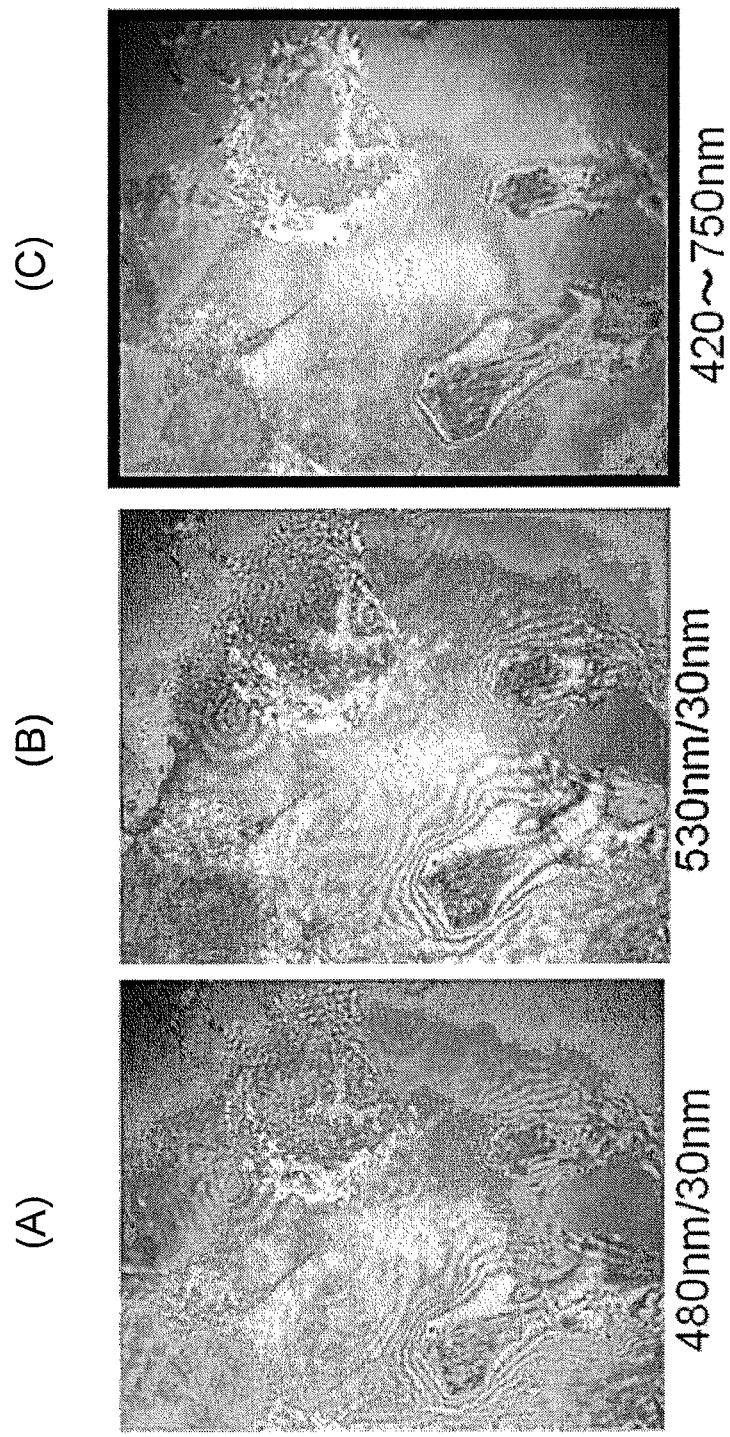
FIG. 6 is a drawing showing reflection interference images differing depending upon difference of wavelength band.

FIG. 6 shows the difference of the reflection interference image with the use of the illumination light having the wide wavelength band of 420 nm to 750 nm from those with the use of the illumination light band-passed in the narrow wavelength band of about 30 nm around the center wavelength of 480 nm or 530 nm. With the illumination light band-passed in the narrow wavelength band as shown in (A) of FIGS. 6 and (B) of FIG. 6, reflection from interfaces between the culture solution and the upper cell membranes of cells different from the adhesion faces of cells is observed like interference fringes over the image, whereas with the use of the illumination light having the wide wavelength band, as shown in (C) of FIG. 6, no interference is observed due to reflected light from the upper parts of cells and thus it becomes feasible to extract only the information more limited to the adhesion faces of cells.

The light source 106 used in the present embodiment is a halogen lamp with a wide band of radiation wavelengths and output light therefrom is passed through a band-pass filter with an arbitrary wide wavelength band in the visible-to-near infrared wavelength zone from about 420 nm to about 800 nm. The reflection interference image can be extracted as being limited to the adhesion faces of cells, with the use of the band-passed light having the center wavelength of 500 nm to 1000 nm and the full width at half maximum of not less than 100 nm. Since the distance between the substrate and a cell adhering to the substrate, is considered to be at most 1 µm or less in the optical-axis direction, it is considered that the excessive interference distance of reflection interference is preferably kept not more than 1 µm in order to specifically extract only information on the adhesion face of each cell to the substrate. Therefore, the illumination light for reflection interference to be radiated is band-passed light through an optical filter so that the wavelength band ranges over about several hundred nm in the region of white light or near infrared light, with exclusion of the ultraviolet region and heat wave region to cause an adverse effect on the cells. When the wavelength band is expanded to shorten the coherence length of light and decrease the coherency distance in this manner, it becomes feasible to extract only interference of reflected light obtained from the adhesion region between the cells and the bottom of the vessel. For example, when the light used is light band-passed in the wide band with the center wavelength of 600 nm and the band width of 200 nm, the coherency distance can be decreased to about 500 nm and it is feasible to extract only interference in the distance of about 500 nm near the adhesion face of each cell.

Referring back to FIG. 1, the ring-shape slit 107 is preferably arranged at the position conjugate with the pupil of the objective lens 104 in the illumination light beam so as to implement annular illumination. In general, it is necessary to measure as many cells as possible in order to acquire statistically significant data. For this purpose, it is preferable to measure a wide field at once with the use of the objective lens having a magnification as low as possible. However, the low-magnification objective lens has a low NA and low-NA illumination light has many components vertically impinging on a sample, which cause a phenomenon in which the light is reflected at an interface between the solution present above a cell and air and the reflected light illuminates the cell. This causes a morphological image of the cell unrelated to an adhesion face thereof to be included on the observation side. The illumination light passing through the central region of the objective lens is reflected inside the objective lens and the reflected light is included in a large quantity on the observation side to become high background light, which causes reduction in contrast of the reflection interference image of the adhesion face.

When the objective lens 104 with a low NA is used in the reflection interference measurement in the membrane potential change detection device 1 according to the present embodiment, the ring-shape slit 107 is disposed at the position conjugate with an aperture stop on the reflection interference measurement light source 106 side of the objective lens 104. The illumination light from the reflection interference measurement light source 106 passes through the slit 107 opening in the ring shape, the illumination light passes through the periphery without passing through the center of the objective lens 104, to illuminate the cells, and the cells 101 are thus illuminated using only angled light with high NA; therefore, it is feasible to reduce influence of the reflected light from the solution above the cells 101. The illumination with the use of the ring-shape slit 107 can reduce not only the reflection due to the low-NA objective lens 104, but also generally the background light due to reflection inside the objective lens 104. For allowing the slit 107 opening in the ring shape to be changed for each objective lens 104 so as to fit the pupil diameter of the objective lens 104 to be used, the device is so configured that a plurality of ring-shape slits 107 fit for respective objective lenses 104 to be used are provided on a disk and the user is allowed to select a ring-shape slit 107 by rotating the disk as occasion may demand. The same effect can also be achieved when the ring-shape slit 107 is located at the position where the pupil of the objective lens 104 itself exists.

Next, the reflection interference measurement will be described. As shown in FIG. 1, the illumination light emitted from the reflection interference measurement light source 106 passes through the ring-shape slit 107, is reflected by the half mirror 108, passes through the objective lens 104, and is incident into the vessel 102 housing the cells 101 as a measurement target, from the bottom side thereof. Without having to be limited to the half mirror, it is also possible to use a beam splitter with a reduced reflection ratio, e.g., 5:95 (reflection:transmission) or 20:80 (reflection:transmission), if the intensity of the illumination light is sufficiently high. It is also possible to use a dichroic mirror with the reflectance and transmittance differing depending upon wavelengths. The reflected light from the adhesion faces of the cells 101 on the bottom surface of the vessel 102 causes interference according to their adhesion distances, the resultant reflection interference light is condensed again by the objective lens 104, and the light travels via the half mirror 108 to be imaged by the reflection interference detection camera 110. In this manner, the light reflected from the adhesion faces of the cells 101 on the bottom surface of the vessel 102 comes to have different amplitudes of interfering light according to the adhesion distances of the cells 101, to be imaged as a contrast of bright and dark patterns.

The principle of reflection interference will be briefly described below. In general, the reflection interference measurement is carried out in such a manner that the illumination light is made incident from the back side of a substrate to which a cell adheres and interference occurs between reflected light from an interface between the substrate and a culture solution and reflected light from an interface between the culture solution above it and a bottom face of the cell to obtain a contrast of bright and dark patterns according to the distance between the cell and the substrate. With illumination of visible light, the cell is photographed as a dark image in a state in which the distance between the cell and the substrate is short, approximately not more than several ten nm. On the other hand, the cell is photographed as a bright image in a state in which the distance between the cell and the substrate is large, approximately 100 nm to 200 nm.

The membrane potential change detection device 1 of the present embodiment may have a mechanism to move the position of observation, in order to measure as many cells 101 as possible or in order to measure a response to different reagents. In order to minimize influence on the cells 101 and suppress vibration of the liquid level in the quantitative phase measurement, it is preferable to adopt a method for changing the observation position by moving the main body of the image acquisition unit 10 as an integrated body of the illumination optical system and the observation optical system on the XY plane, while keeping the vessel housing the cells 101 stationary. In conjunction therewith, it is preferable to record plane coordinates in the XY space under observation on images. In the present embodiment, the device is equipped with the XY stage 115 the moving distance of which fully covers the observation range of the vessel 102 and the positioning accuracy of which is several ten μm or below (preferably, 1 μm or below).

(Description of Processing Unit 20).

Figure 7:
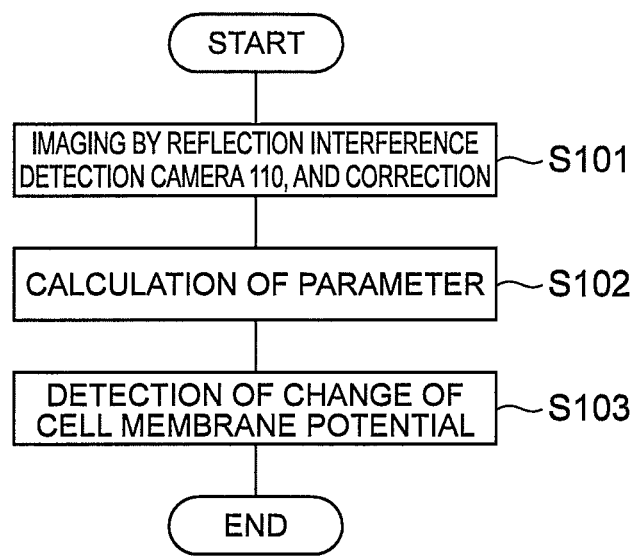
FIG. 7 is a flowchart showing functions and operation of the processing unit.

The functions and operation of the processing unit 20 will be described further referring to the flowchart of FIG. 7. First, the reflection interference image of adhesion faces of cells 101 is obtained by the reflection interference detection camera 110 (step S101, corresponding to "reflection interference imaging step" in the scope of claims). The amplitude of interfering light differs according to the distance of each cell 101 adhering onto the substrate as the bottom surface of the vessel 102 from the substrate as the bottom surface of the vessel 102, and the reflection interference image is taken as a contrast of bright and dark patterns. Next, correction is made for shading of reflected light in the field of the reflection interference image. In addition, an offset correction for background part is carried out in each time unit, so as to prevent temporal variation in value of the background without the cells 101. Through these image arithmetic corrections, we can obtain the reflection interference image with little spatial and temporal variation.

The reflection interference detection camera 110 acquires reflection interference images, for example, at intervals of one second. The intervals of acquisition of reflection interference images are preferably suitably controlled according to a rate of change of membrane potential of the cells 101. After a fixed time from a start of acquisition of image by the reflection interference detection camera 110, a chemical dispensing operation of the dispenser 117 is performed to dispense an intended chemical in an intended concentration to the solution in which the cells 101 are immersed.

The analysis unit 202 calculates a parameter about adhesion between each cell 101 and the transparent member 102a using the reflection interference images obtained intermittently in this manner (step S102, corresponding to "analysis step" in the scope of claims). In the present embodiment, the analysis unit calculates a "change rate of average luminosity" as the parameter to evaluate the change of membrane potential of cell 101 (corresponding to "parameter about adhesion" in the scope of claims). The analysis unit 202 differentiates a region where the cells 101 adhere from a region where the cells 101 do not adhere, in a reflection interference image, to specify the region where the cells 101 adhere, and calculates an average luminosity of the region (which will be referred to hereinafter as "measurement region").

When the image reception unit 201 receives the reflection interference images sequentially output from the reflection interference detection camera 110, the analysis unit 202 calculates the average luminosity I(t) of the measurement region in each of the reflection interference images and calculates a change rate dI relative to an average luminosity of the measurement region acquired in advance before chemical dispensation (which will be referred to hereinafter as average luminosity I(base) as a base") (step S103, corresponding to "analysis step" in the scope of claims). The average luminosity as a base may be, for example, an average luminosity obtained from the reflection interference images of the measurement region acquired before chemical dispensation, or a default luminosity stored in advance as a default value for each type of cell. Such an average luminosity as a base is stored in the storage unit 203 and the analysis unit 202 retrieves the average luminosity as a base timely from the storage unit 203 and calculates the change rate dI. The change rate dI is calculated by the formula below.

Change rate $dI(t)=\{I(t)-I(\text{base})\}/I(\text{base})$

I(t)=average luminosity of reflection interference (value after background correction)

I(base)=average of I(t) before chemical dispensation

The analysis unit 202 detects a change of membrane potential of the cells 101 on the basis of the change rate dI calculated by the above formula. Namely, when a predetermined change rate dI is calculated, the analysis unit 202 makes such a valuation that there is some change detected in membrane potential in the cells 101. The analysis unit 202 may output a plot along time axis of the change rate dI (%) relative to the average luminosity before chemical dispensation calculated by the above formula, e.g., graphs as shown in (A) of FIGS. 8 and (B) of FIG. 8. Namely, a graph as a plot of change rate dI (%) relative to the luminosity before chemical dispensation may be output as a graph indicative of a change of membrane potential of the cells 101.

The membrane potential change detection device 1 of the present embodiment is based on the correlation such that when depolarized, the cells 101 depart from the transparent member 102a to make the reflection interference image brighter and when hyperpolarized, the cells 101 approach the transparent member to make the reflection image darker. Therefore, it is feasible to detect depolarization of membrane potential of the cells 101 by a change in the positive direction of the change rate dI and to detect hyperpolarization of membrane potential of the cells 101 by a change in the negative direction of the change rate dI. The device is also able to find a peak (a maximum in the case of depolarization or a minimum in the case of hyperpolarization) within a certain period after chemical dispensation and to make a determination on a concentration of a chemical dispensed to the cells 101 from the magnitude of the numerical value. This will be described in the sections of Measurement Examples 1 and 2 below.

After completion of an analysis on one well, the membrane potential change detection device 1 moves the XY stage 115 to a position of another well to be measured next, and again starts the measurement with focus on the mount surface 102b of the cells 101. This operation is repeated to measure reactions of the cells 101 to various types of chemicals.

Measurement Example 1

In this example, the vessel 102 housing CHO cells (Chinese hamster ovary cells) was set on the holder 103 and KCl (chemical: potassium chloride) to cause depolarization in the CHO cells was dispensed to examine the reflection interference images acquired by the reflection interference detection camera 110 and the change rate dI (parameter) of average luminosity calculated by the analysis unit 202.

Figure 9:
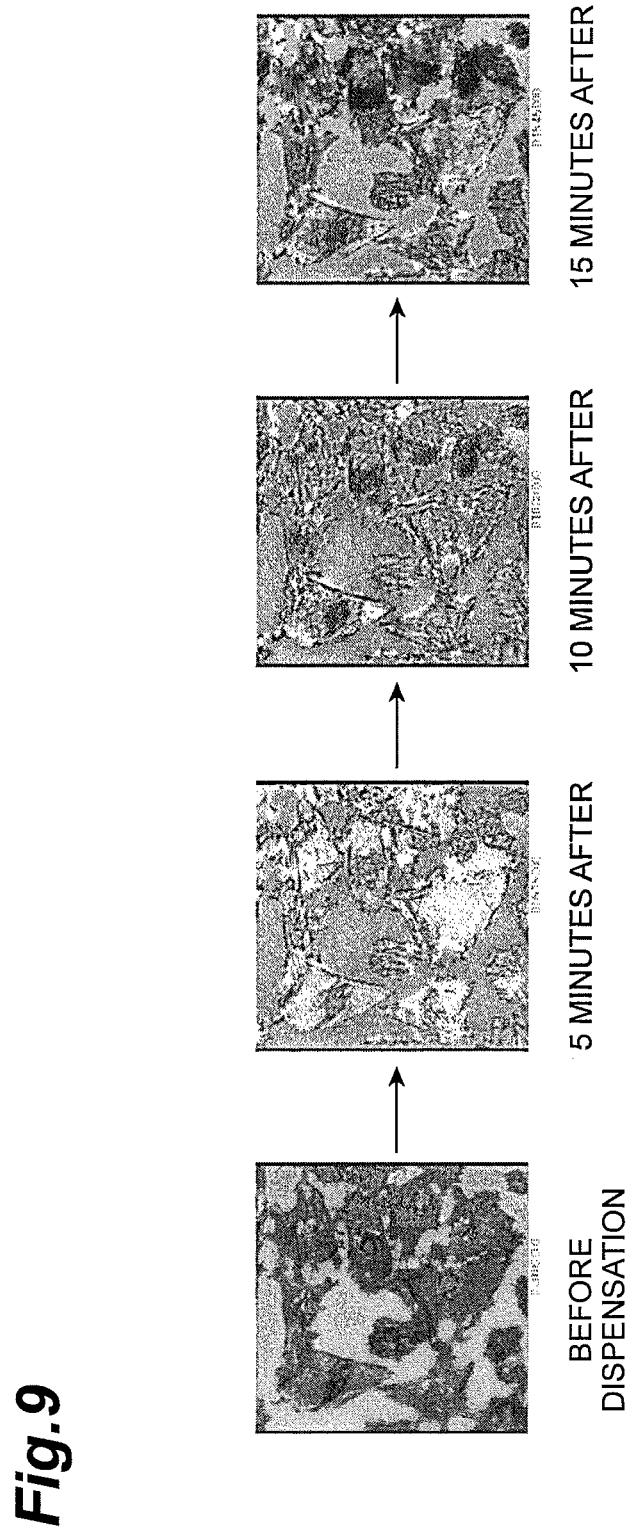
FIG. 9 is a drawing showing change of reflection interference images in Measurement Example 1.

First, we examined the reflection interference images before dispensation of KCl to the CHO cells, at 5 minutes after dispensation of KCl, at 10 minutes after dispensation of KCl, and at 15 minutes after dispensation of KCl, which were acquired by the reflection interference detection camera 110. It was observed by this examination that after the dispensation of KCl to the CHO cells, as shown in FIG. 9, there occurred a departure phenomenon in which the CHO cells departed from the transparent member on which the cells were laid, to make the reflection interference image brighter (the image at 5 minutes after). This confirmed that the membrane potential change detection device 1 of the present embodiment was able to detect depolarization of membrane potential of the cells 101, for example, by calculating the "change rate dI of average luminosity" as a parameter (parameter about adhesion) to evaluate a change of membrane potential of the cells 101 and detecting a change of the parameter.

Figure 10:
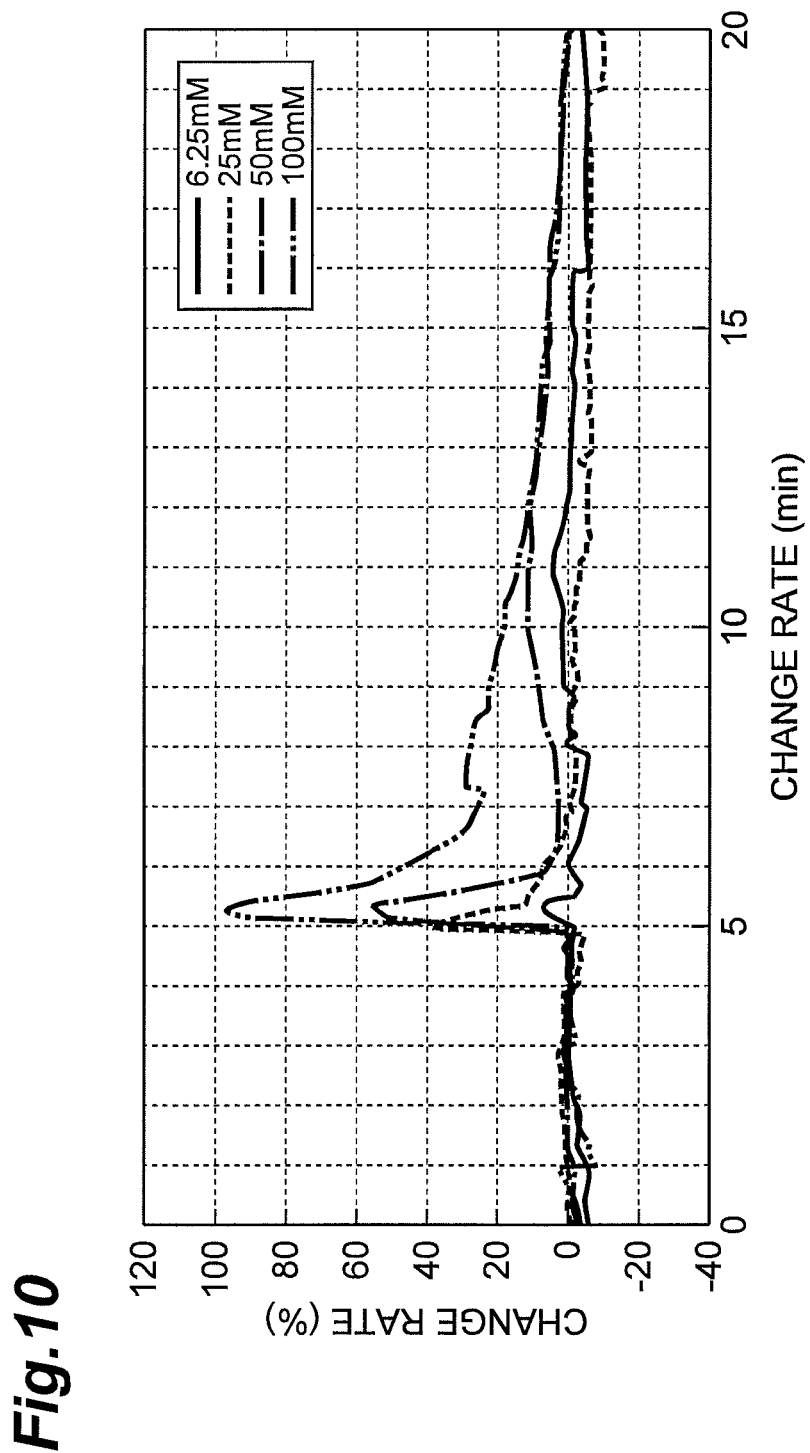
FIG. 10 is a graph showing temporal changes of change rate in Measurement Example 1.

Next, KCl was dispensed in each of different concentrations (6.25 mM, 25 mM, 50 mM, or 100 mM) to the CHO cells and the analysis unit 202 calculated the change rate dI of average luminosity (parameter) for each case. As a result, we obtained a graph as shown in FIG. 10. It was confirmed by this result that as the membrane potential of cells 101 turned to depolarization, the change rate dI of average luminosity transiently changed in the positive direction. In the membrane potential change detection device 1 of the present embodiment, therefore, the analysis unit 202 can detect the transient increase in the positive direction of the change rate dI of average luminosity, as shown in FIG. 10, and thus the device is able to detect the depolarization of membrane potential of the cells 101.

Figure 11:
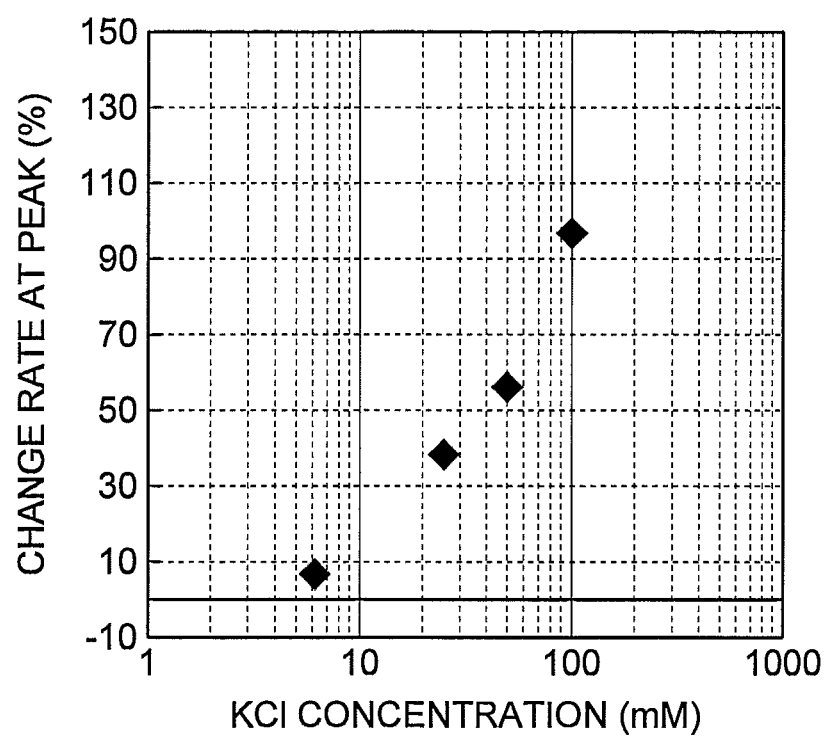
FIG. 11 is a graph showing a relation of concentration versus change rate at peak in Measurement Example 1.

It was also confirmed from the graph of FIG. 10 that the change rate dI of average luminosity increased the maximum amplitude in the positive direction in proportion to the concentration of KCl dispensed. Then a graph was made for a relation of change rate dI of average luminosity against concentration of KCl at a peak of change rate dI of average luminosity (upon a lapse of time slightly over five minutes in FIG. 10) and we obtained the result, as shown in FIG. 11, that the change rate of average luminosity at the peak increased in the order of +8%, +35%, +55%, and +95% with increase in the KCl concentration of 6.25 mM, 25 mM, 50 mM, and 100 mM. It was confirmed by this result that there was a dependence relationship between the change rate of average luminosity at the peak and the concentration of the chemical dispensed. Since the membrane potential change detection device 1 of the present embodiment calculates the change rate dI of average luminosity proportional to the concentration of the chemical dispensed (or dependent on the concentration), it is able to evaluate the change of membrane potential of the cells 101 in each concentration of the chemical dispensed. For this reason, it becomes feasible to apply the membrane potential change detection device 1 of the present embodiment to cases of evaluation of drug efficacy on the cells 101.

Measurement Example 2

In this example, an active compound was dispensed to calcium-dependent potassium channels using an MIN-6 pancreatic β cell line (mouse-derived pancreatic β cell line) (which will be referred to hereinafter as "sample cells"), to examine the reflection interference images acquired by the reflection interference detection camera 110 and the change rate dI of average luminosity (parameter) calculated by the analysis unit 202.

Figure 12:
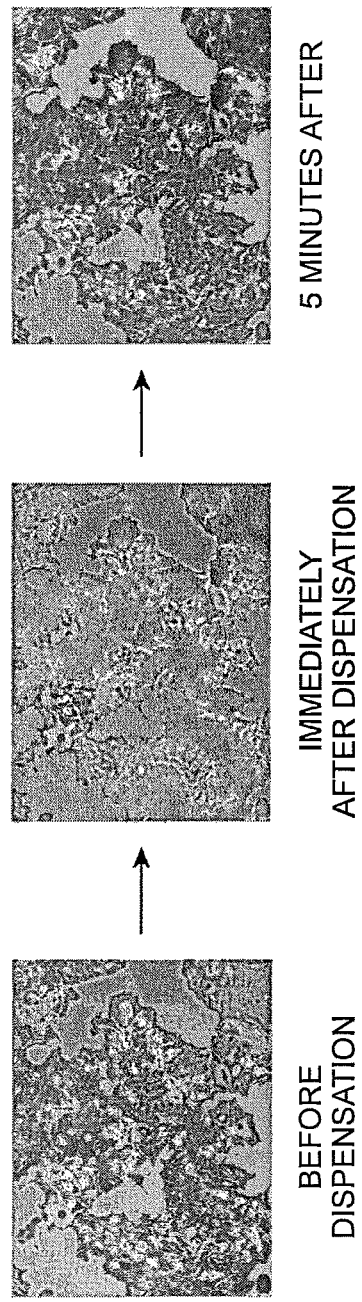
FIG. 12 is a drawing showing change of reflection interference images in Measurement Example 2.

First, we examined the reflection interference images before dispensation of the active compound to the sample cells, immediately after the dispensation of the active compound, and at 5 minutes after the dispensation of the active compound, which were acquired by the reflection interference detection camera 110. It was observed by this examination, as shown in FIG. 12, that after dispensation of the active compound to the sample cells, there occurred an approach phenomenon in which the sample cells approached to the transparent member on which the cells were laid, to make the reflection interference image darker (the image immediately after dispensation of the active compound). It was confirmed by this result that the membrane potential change detection device 1 of the present embodiment was able to detect the hyperpolarization of membrane potential of the cells 101, for example, by calculating the "change rate dI of average luminosity" as a parameter (parameter about adhesion) to evaluate a change of membrane potential of the cells 101, and detecting a change of the parameter.

Figure 13:
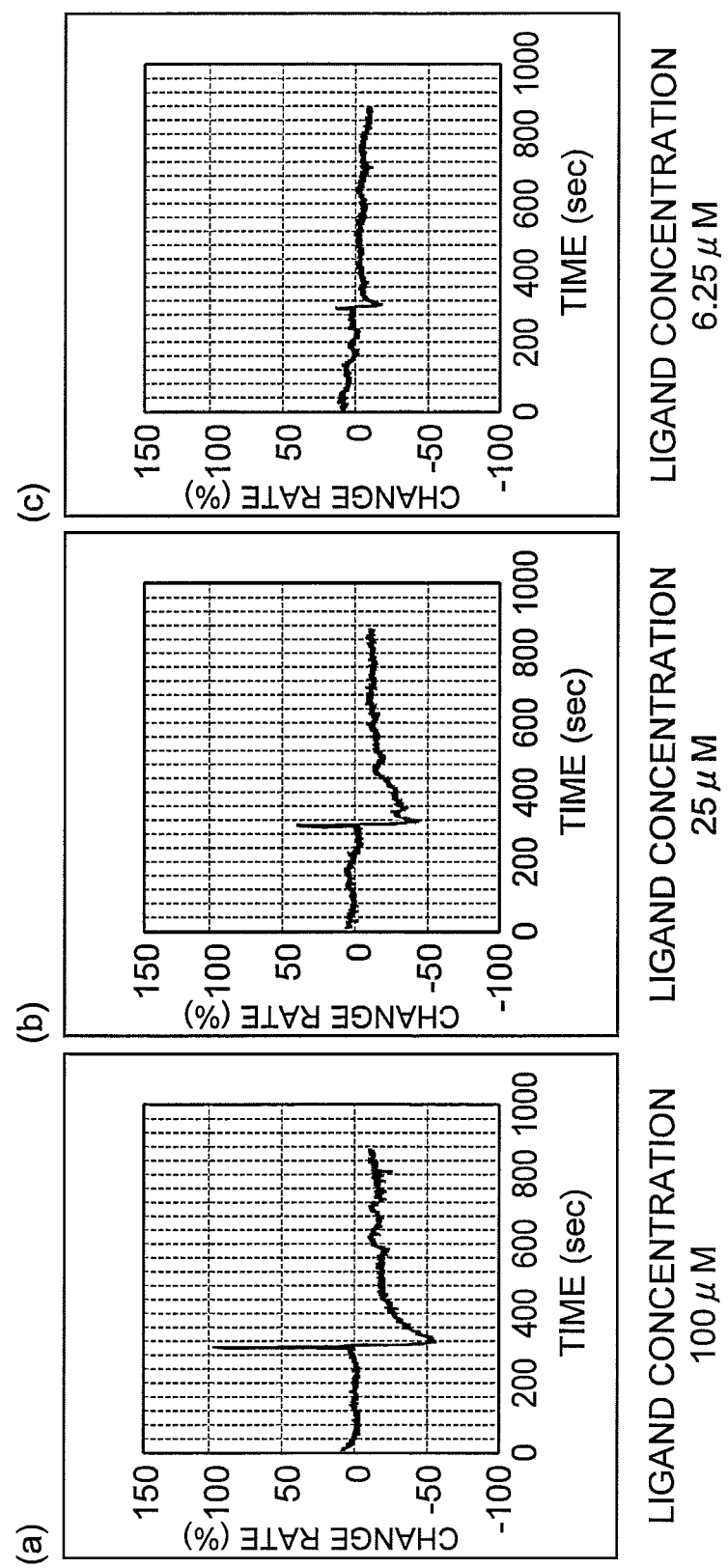
FIG. 13 is graphs showing temporal changes of change rate in Measurement Example 2.

Next, the active compound was dispensed in each of different ligand concentrations (100 μM, 25 μM, or 6.25 μm) to the sample cells and the analysis unit 202 calculated the change rate dI of average luminosity (parameter) for each case. As a result, we obtained graphs of the respective cases as shown in FIG. 13. It was confirmed by this result that as the membrane potential of cells 101 turned to hyperpolarization, the change rate dI of average luminosity transiently changed in the negative direction. In the membrane potential change detection device 1 of the present embodiment, therefore, the analysis unit 202 can detect the transient increase in the negative direction of the change rate dI of average luminosity, as shown in FIG. 13, and thus the device is able to detect the hyperpolarization of membrane potential of the cells 101.

Figure 14:
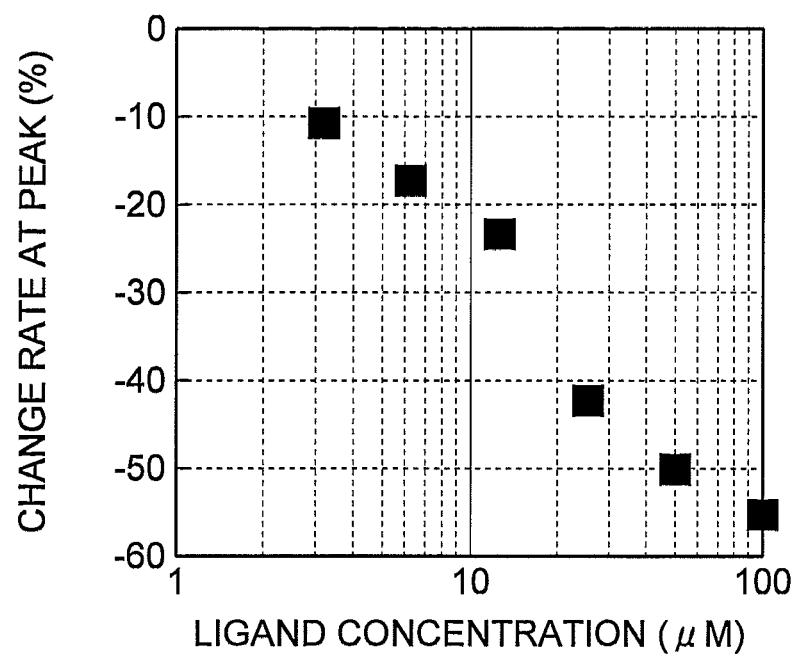
FIG. 14 is a graph showing a relation of concentration versus change rate at peak in Measurement Example 2.

It was confirmed by summing up the graphs in FIG. 13 that the change rate dI of average luminosity increased the maximum amplitude in the negative direction in proportion to the concentration of the active compound dispensed. Then a graph was made for a relation of change rate dI of average luminosity against concentration of the active compound at a peak of the change rate dI of average luminosity (around 300 milliseconds in FIG. 13) and we obtained the result, as shown in FIG. 14, that a change amount in the negative direction of the change rate dI of average luminosity after dispensation of the chemical increased in the order of 10%, 17%, 23%, 42%, 49%, and 55% with increase in the concentration of the active compound of 6.25 μM, 25 μM, and 100 μM. It was confirmed by this result that there was a dependence relationship between the change rate of average luminosity at the peak and the concentration of the chemical dispensed. Since the membrane potential change detection device 1 of the present embodiment calculates the change rate dI of average luminosity proportional to the concentration of the chemical dispensed (or dependent on the concentration), it is able to evaluate the change of membrane potential of the cells 101 in each concentration of the chemical dispensed. For this reason, it becomes feasible to apply the membrane potential change detection device 1 of the present embodiment to cases of evaluation of drug efficacy on the cells 101.

Operation and Effects of First Embodiment

The below will describe the operation and effects of the membrane potential change detection device 1 of the first embodiment described above. The membrane potential change detection device 1 of the present embodiment is provided with the reflection interference measurement light source 106, the holder 103, the reflection interference detection camera 110, and the analysis unit 202, whereby the device calculates the parameter about adhesion between the cells 101 and the transparent member 102*a* on the basis of the reflected light from the cells 101 and detects the change of membrane potential of the cells 101 on the basis of the change of the parameter. The inventors discovered that there was the correlation between the degree of adhesion between the transparent member on which the cells were laid, and the cells, and the change of membrane potential of the cells. The present invention is characterized in that the change of membrane potential of cells is defined as a change in adhesion distance (adhesion degree) between the cells and the transparent member, by making use of the aforementioned correlation discovered. Since the parameter about adhesion between cells 101 and transparent member 102*a* based on the adhesion distance is obtained by a non-invasive method, the change of membrane potential of cells 101 can be non-invasively detected without labeling.

The membrane potential change detection device 1 is able to detect the change of membrane potential of the cells 101 when the cells 101 become depolarized and hyperpolarized.

Modification Example of First Embodiment

The above embodiment was described using the example in which the "measurement region" was the region where the cells 101 adhered, as a measurement region as an analysis target for evaluation on the change of membrane potential of the cells 101, but the present invention is not limited to this example. For example, cells 101 were cultivated in a confluent manner (about 80% to the area of the vessel) to prepare a specimen, and an entire field of a reflection interference image obtained at a start of measurement may be defined as a measurement region. Furthermore, a region where the cells 101 are present, which was extracted by use of a fixed luminosity threshold or image processing from the reflection interference image obtained at a start of measurement, may be defined as a measurement region.

The above embodiment was described using the example in which the "change rate of average luminosity" was used as the parameter to evaluate the change of membrane potential of the cells 101, but the present invention is not limited to this example. For example, it is also possible to use a "change in increase or decrease of adhesion area" as a parameter to evaluate the change of membrane potential of the cells 101. In this case, the measurement region is defined as a region corresponding to adhesion of the cells 101, which was extracted by use of a certain luminosity threshold or image processing from the reflection interference images acquired in time series, and the number of pixels in the measurement region is determined over the entire field. In this case a change rate dA of increase/decrease of adhesion area is calculated by the formula below.

Change rate $dA(t)=\{A(t)-A(\text{base})\}/A(\text{base})$

A(t)=the number of pixels in an adhesion region at each time of reflection interference A(base)=average of A(t) before chemical dispensation The analysis unit 202 detects the change of membrane potential of the cells 101 on the basis of the change rate dA calculated by the above formula. Namely, when a predetermined change rate dA is calculated, the analysis unit 202 may make such a valuation that there is some change detected in membrane potential in the cells 101. The analysis unit 202 may output a graph of a plot along time axis of the change rate dA calculated by the above formula, as a graph indicating the change of membrane potential of the cells 101. Namely, it may output a graph of a plot of the change rate dA (%) to the adhesion area before chemical dispensation, as a graph indicating the change of membrane potential of the cells 101. This allows the change of membrane potential of the cells 101 to be clearly shown for the user using the membrane potential change detection device 1.

As described above, since the membrane potential change detection device 1 of the present embodiment is based on the correlation such that when depolarized, the cells 101 depart from the transparent member 102a and when hyperpolarized, the cells 101 approach the transparent member, it is able to detect the depolarization of cells 101 in membrane potential by the change in the positive direction of the change rate dA and to detect the hyperpolarization of membrane potential of cells 101 by the change in the negative direction of the change rate dA. The present modification example is also the same in that the device is able to find a peak in a fixed period after the dispensation of a chemical (a maximum in the case of depolarization or a minimum in the case of hyperpolarization) and make a determination on the concentration of the chemical dispensed to the cells 101 from the magnitude of the numerical value.

Second Embodiment

The second embodiment of the present invention will be described. The second embodiment will be described in detail as to only the configuration different from the first embodiment and the same configuration as in the first embodiment will be denoted by the same reference signs, without detailed description thereof.

(Overall Configuration of Membrane Potential Change Detection Device 41)

Figure 15:
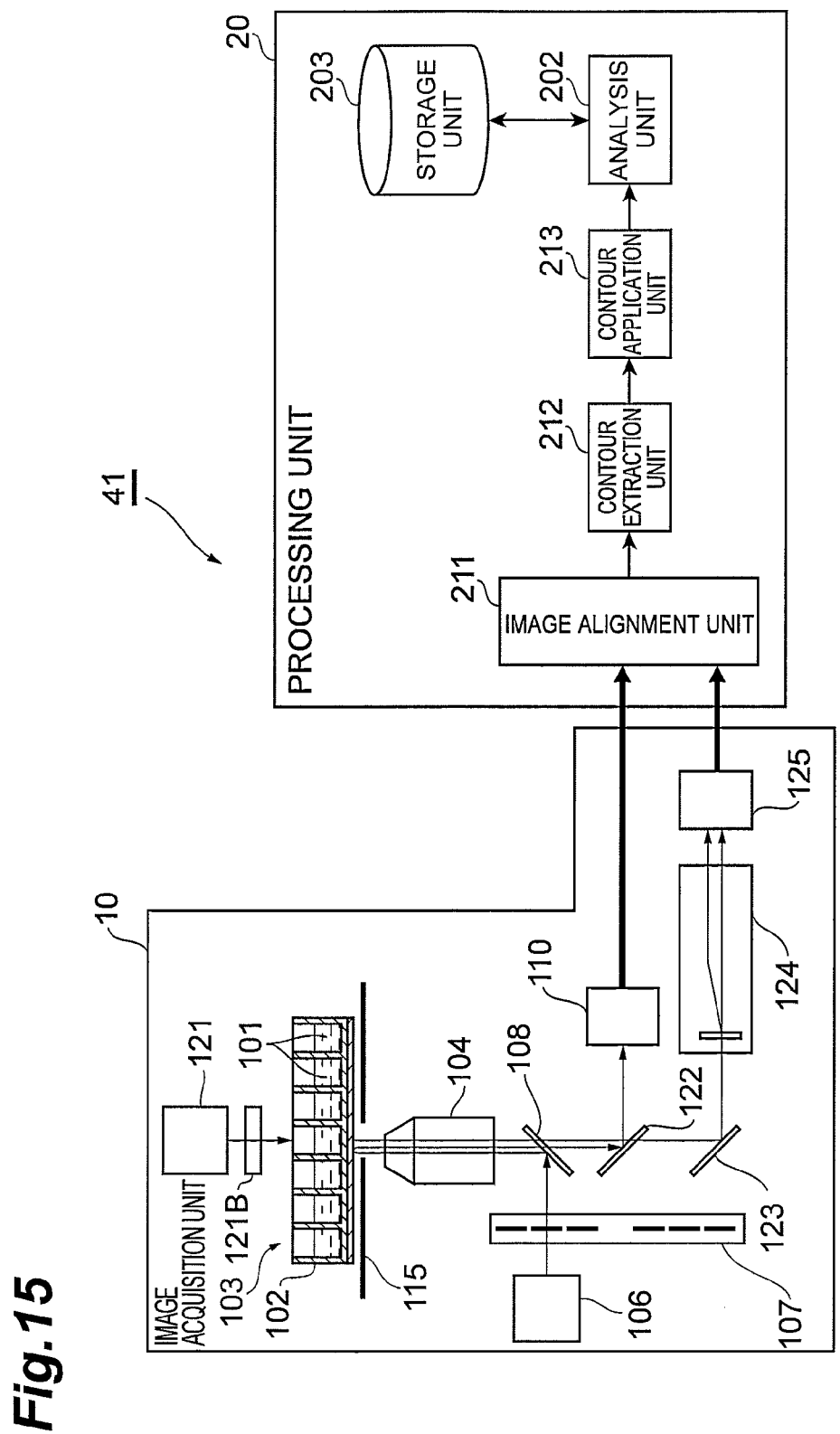
FIG. 15 is a schematic diagram showing an overall configuration of a membrane potential change detection device according to the second embodiment.

First, an overall configuration of a membrane potential change detection device 41 according to an embodiment of the present invention will be described with reference to FIG. 15. FIG. 15 is a schematic diagram showing the overall configuration of the membrane potential change detection device 41. As shown in FIG. 15, the membrane potential change detection device 41 is composed of the image acquisition unit 10 and the processing unit 20.

The image acquisition unit 10 is provided with the holder 103 (corresponding to "holding means" in the scope of claims), the objective lens 104, a quantitative phase measurement light source 121, an illumination stop unit 121B, the reflection interference measurement light source 106, the half mirror 108, a dichroic mirror 122, a total reflection mirror 123, the reflection interference detection camera 110 (corresponding to "reflection interference imaging means" in the scope of claims), a diffractive interference optical system 124, and a quantitative phase detection camera 125 (corresponding to "quantitative phase imaging means" in the scope of claims). The half mirror 108 is a reflection interference incidence optical system for guiding the light from the reflection interference measurement light source 106 to the cells 101 and the dichroic mirror 122 is a reflection interference measurement optical system for guiding the light from the cells 101 to the reflection interference detection camera 110. The objective lens 104, the half mirror 108, and the dichroic mirror 122 constitute a common optical system for guiding light from an identical range of cells 101 to the reflection interference detection camera 110 and to the quantitative phase detection camera 125. Namely, in the present embodiment the reflection interference incidence optical system and the reflection interference measurement optical system are a common optical system. Furthermore, the total reflection mirror 123 and the diffractive interference optical system 124 constitute a quantitative phase optical system for guiding light to the quantitative phase detection camera 125. The reflection interference detection camera 110 images the light emitted from the reflection interference measurement light source 106 and reflected from the cells 101, to generate a reflection interference image. The quantitative phase detection camera 125 images the light emitted from the quantitative phase measurement light source 121 and transmitted through the cells 101, to generate a quantitative phase image. The illumination stop unit 121B is a means to stop the illumination light. The illumination stop unit 121B can be a pinhole or an aperture as an example.

The processing unit 20 is provided with an image alignment unit 211 (corresponding to "image alignment means" in the scope of claims), a contour extraction unit 212 (corresponding to "contour extraction means" in the scope of claims), a contour application unit 213 (corresponding to "contour application means" in the scope of claims), an analysis unit 202 (corresponding to "analysis means" in the scope of claims), and a storage unit 203.

The image alignment unit 211 is a part that matches a spatial position of the reflection interference image with a spatial position of the quantitative phase image to achieve alignment between the two images. The contour extraction unit 212 is a part that extracts contours as ranges of the cells 101, based on the quantitative phase image. The contour application unit 213 is a part that applies the contours extracted by the contour extraction unit 212, to the reflection interference image to generate a reflection interference image after contour application. The analysis unit 202 is a part that calculates a parameter of each cell 101 about adhesion between the cell 101 and the transparent member 102a, based on the reflection interference image after contour application, and detects a change of membrane potential of each cell 101 on the basis of a change of the parameter. FIG. 2 is a hardware configuration diagram of the processing unit 20 provided with the functional constituent elements as described above. Since the hardware configuration is the same as in the case of the membrane potential change detection device 1 of the first embodiment, the description thereof is omitted herein.

Next, the image acquisition unit 10 will be described in detail with reference to FIG. 15. The quantitative phase measurement will be described. The illumination light emitted from the quantitative phase measurement light source 121 such as a halogen lamp or a xenon lamp, which is installed above the vessel 102 housing the cells 101, passes through the illumination stop unit 121B such as a pinhole or an aperture to become illumination light close to a point light source, and then the illumination light passes through the vessel 102 housing the cells 101, to be condensed by the objective lens 104. The quantitative phase measurement light source 121 to be used may be a light source such as an LED (light emitting diode), a semiconductor laser (laser diode), or an SLD (super luminescent diode). In the case of the laser or the SLD, the illumination stop unit 121B does not have to be provided because the light source size is sufficiently small. Then the light travels via the half mirror 108, passes through the dichroic mirror 122 for separation of the quantitative phase image and the reflection interference image by wavelengths, and further travels via the total reflection mirror 123 to form an interference image between object light and reference light in the diffractive interference optical system 124 for phase measurement, and the interference fringe image is taken by the quantitative phase detection camera 125. The dichroic mirror 122 may be a beam splitter such as a half mirror, and in this case, a filter for selection of wavelengths to be used in quantitative phase detection is disposed between the beam splitter and the quantitative phase detection camera 125.

The reflection interference measurement will be described. The illumination light emitted from the reflection interference measurement light source 106 is reflected by the half mirror 108, and then travels through the objective lens 104 to enter the vessel 102 with the cells 101 as a measurement target therein, from the bottom side thereof. Without having to be limited to the half mirror, a beam splitter with a reduced reflection ratio, e.g., 5:95 (reflection:transmission) or 20:80 (reflection:transmission), may also be used if the intensity of the illumination light is sufficiently high. It is also possible to use a dichroic mirror with the reflectance and transmittance differing depending upon wavelengths. Reflected light from adhesion faces of the cells 101 on the bottom of the vessel 102 causes interference according to adhesion distances of the cells 101, and the resultant reflection interference light is condensed again by the objective lens 104 and travels via the half mirror 108; only the reflection interference image is reflected by the dichroic mirror 122 for separation of the quantitative phase image and the reflection interference image by wavelengths, and picked up by the reflection interference detection camera 110. When a beam splitter such as a half mirror is used instead of the dichroic mirror 122, a filter for selection of the wavelengths to be used in reflection interference detection is to be placed between the beam splitter and the reflection interference detection camera 110. The light reflected from the adhesion faces of the cells 101 on the bottom of the vessel 102 has different amplitudes of interfering light depending upon the adhesion distances of the cells 101 and is imaged as a contrast of bright and dark patterns. Since the quantitative phase image and the reflection interference image are acquired through the common objective lens 104, the imaging range of the cells 101 is approximately the same in the quantitative phase measurement and the reflection interference measurement.

The camera 125 to acquire the quantitative phase image and the camera 110 to acquire the reflection interference image do not have to be limited to cameras of the same performance and same pixel resolution. Since quantities and wavelengths of the light beams incident into the respective cameras are different from each other, they may be cameras of performances and spatial resolutions suitable for the respective operations. For example, the quantitative phase detection camera 125 may be a sensitivity-priority camera with high sensitivity to 830 nm and with a large pixel size, and the reflection interference detection camera 110 may be a spatial-resolution-priority camera with high sensitivity to the visible range and with a small pixel size. This configuration requires a process of matching spatial coordinates of the two cameras, and this process will be detailed later on.

In order to allow discrimination between the quantitative phase measurement and the reflection interference measurement by wavelengths, beams in different wavelength bands may be used for the respective illumination wavelengths of the reflection interference measurement light source 106 and the quantitative phase measurement light source 121. The dichroic mirror 122 can separate and select the quantitative phase image and the reflection interference image by the specific wavelengths. Accordingly, it becomes feasible to obtain the images at the same time without crosstalk by the quantitative phase measurement and the reflection interference measurement.

Figure 16:
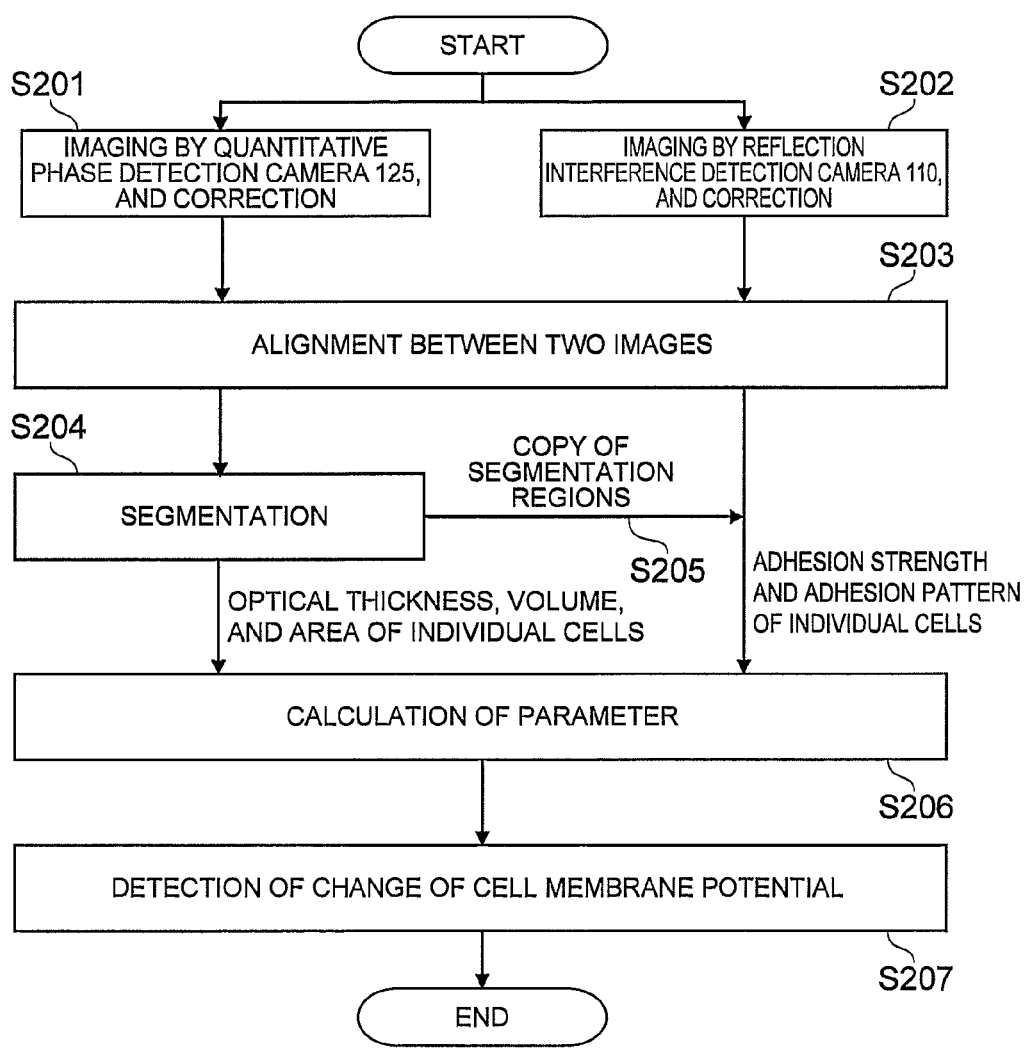
FIG. 16 is a flowchart showing functions and operation of the processing unit according to the second embodiment.

Next, the functions and operation of the processing unit 20 will be described further referring to the flowchart of FIG. 16. First, the quantitative phase detection camera 125 acquires the interference fringe image between reference light and object light having passed through the cells 101 (step S201, corresponding to "quantitative phase imaging step" in the scope of claims). A quantitative phase image is formed from the interference fringe image by a well-known arithmetic method. For obtaining the quantitative phase image, an offset correction of the background region without the cells 101 and a shading correction in the field of the background region are carried out to make the background part spatially uniform and correct the phase value of the background part to 0, thereby obtaining a two-dimensional map of phases (optical path lengths) of the cells 101.

On the other hand, in parallel with the step S201, the reflection interference detection camera 110 acquires the reflection interference image of adhesion faces of the cells 101 (step S202, corresponding to "reflection interference imaging step" in the scope of claims). Since amplitudes of interfering light are different depending upon distances of the cells 101 adhering onto the substrate as the bottom surface of the vessel 102, from the substrate as the bottom surface of the vessel 102, the reflection interference image is taken as a contrast of bright and dark patterns. Correction is made for shading of reflected light in the field of the reflection interference image. At the same time an offset correction for the background part is carried out in each time unit, in order to prevent background values of the background without the cells 101 from varying with time. Through these image arithmetic corrections, we can obtain the quantitative phase image and the reflection interference image with little spatial and temporal variations.

Figure 17:
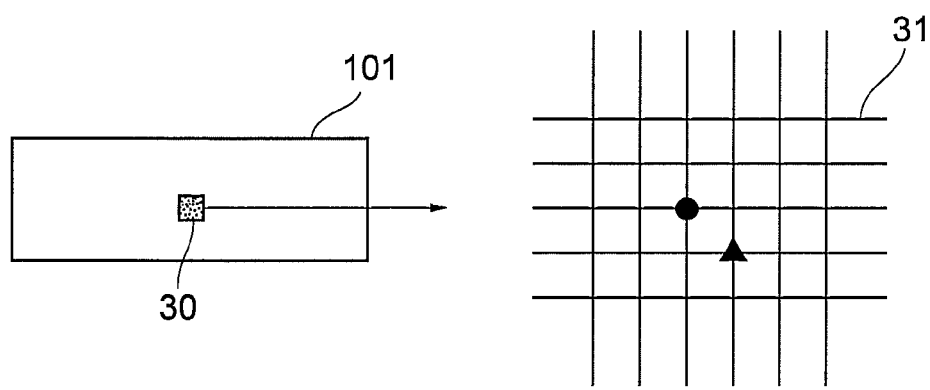
FIG. 17 is a drawing showing a sample used in image alignment in the second embodiment.

The next step is to perform a correction for spatial positions of the quantitative phase image and the reflection interference image (step S203, corresponding to "image alignment step" in the scope of claims). FIG. 17 shows a sample 30 used in image alignment. The sample 30 for alignment to be used herein can be a micro scale in which a grid 31 is scribed on a glass substrate, or a dot pattern. When the micro scale or the dot pattern is provided with at least one mark to identify the same position on images taken by the two cameras, the operation becomes simpler. In the example of FIG. 17, there are two marks, a triangle and a dot.

A procedure for shifting the image of the reflection-interference-side camera 110 so as to be aligned in position with the quantitative phase image will be described below in detail. First, the micro scale or the dot pattern is placed instead of the sample of cells 101 and is taken by each of the taking cameras for the reflection interference and the quantitative phase. Next, a reflection interference image and a quantitative phase image obtained by the photography of the micro scale or the dot pattern are superimposed on each other in respective different false colors (e.g., green for the reflection interference image and red for the quantitative phase image). In some cases the images become easily viewable with inversion of luminance thereof. Next, in order to match the grid image or dot image of the reflection interference image with the grid image or dot image of the quantitative phase image, while viewing the superimposed images, the reflection interference image is finely adjusted in (1) enlargement/reduction ratio, (2) horizontal movement amount (number of pixels), (3) vertical movement amount (number of pixels), (4) angle of rotation, (5) direction of rotation, (6) mirror reversal, etc. to determine adjustment amounts thereof. The adjustment amounts can be determined to achieve such position that the grid images or dot images displayed in superposition overlap each other with no edges projecting out, for example, such position that the grid images or dot images overlap each other to turn green and red into yellow.

If the two camera images taken have spatial distortions and patterns of the spatial distortions of the two images are largely different, it is sometimes difficult to equally match the positions of all the pixels by the aforementioned data (1) to (6) only. In such cases movement amounts are different for all the pixels in the field and it is thus necessary to determine the movement amounts for the respective pixels. Specifically, shift amounts of respective points are determined so as to match intersections of the grid images or center coordinates of respective dots of the dot images with each other between the two cameras. Shift amounts for spatial coordinates except for the coordinates where the grid or dots exist are determined by interpolation. A table is created by storing the shift amounts in pixel unit for spatially all pixels (all coordinates) in this manner, and is defined as alignment data. The alignment data thus obtained is stored as a file. When new measurement is performed to acquire images, alignment between the images is carried out using the alignment data stored in the file, and position-corrected images are output. When the image data acquired through execution of new measurement is stored in a file, the alignment data is preferably stored together with the image data in the file. This allows the device to quote the alignment data, which was the best in new acquisition of the images, in calling of the image file and to correct the called images.

The alignment as described above does not have to be performed every measurement of quantitative phase and reflection interference, but may be performed, for example, at the frequency of once per month, with consideration to positional deviation due to influence of the use environment and vibration, as long as the same optical system is used. If the observation-side optical system is equipped with a component to select a filter for observation (e.g., an electric filter wheel), the alignment is preferably performed for each filter to be used. The reason for it is that positional deviation amounts and directions of positional deviation of images differ depending upon inclination or parallelism of the filter to be used.

Although description is omitted to avoid redundancy, the above procedure can also be suitably applied to the case opposite to the above, i.e., the case where the image of the quantitative-phase-side camera 125 is shifted in position so as to match the reflection interference image. The above procedure can be carried out without the aid of human hand by automated image processing.

Referring back to FIG. 16, after the alignment in the step S203, a process of extracting contour regions of the cells 101 (which will also be referred to hereinafter as "segmentation") is carried out (steps S204 and S205, corresponding to "contour extraction step" in the scope of claims).

Figure 18:
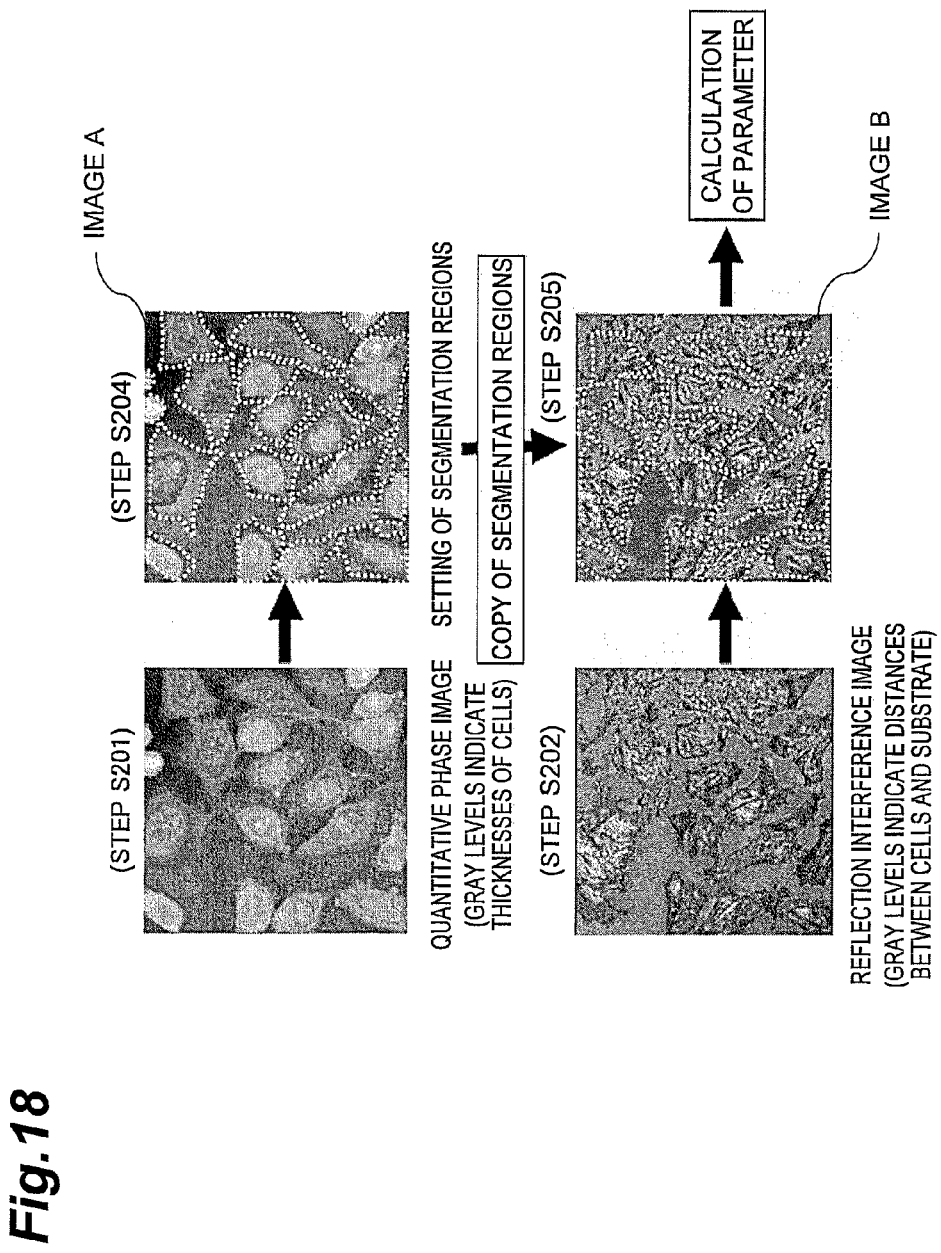
FIG. 18 is a drawing showing an example of a contour extraction process and a contour application process according to the second embodiment.

First, as shown in FIG. 18, regions as contours of individual cells 101 are detected from the quantitative phase image out of the quantitative phase image and the reflection interference image after taken at the same time and aligned with each other, by image processing (step S204, corresponding to "contour extraction step" in the scope of claims). Namely, in the quantitative phase image, the optical path lengths of light passing through the cells 101 become longer than those of light passing through the solution as the background without the cells 101 therein, because the refractive index of the cells 101 is larger than that of the solution. For this reason, phase values of pixels in the regions where the cells 101 exist become larger than those in the background. Therefore, when an appropriate threshold or spatial filtering process is applied, the cells 101 can be separated from the background automatically without the aid of human hand. Then the contours corresponding to the respective cells 101 can be determined and regions of pixel coordinates corresponding to the regions occupied by the respective cells 101 can be determined.

Next, the pixel coordinates of the contour regions of the individual cells 101 obtained in step S204 are adapted to the reflection interference image aligned in spatial coordinates, i.e., the segmentation regions obtained in step S204 are copied onto the reflection interference image, whereby the contour regions of the individual cells 101 determined on the quantitative phase image are applied to the reflection interference image (step S205, corresponding to "contour application step" in the scope of claims). By this step, as shown in FIG. 18, the same contour regions can be determined for the two images A, B of the quantitative phase image and the reflection interference image. Furthermore, it is feasible to determine the contour corresponding to each cell and to determine the region of pixel coordinates corresponding to the region occupied by each cell.

Referring back to FIG. 16, the analysis unit 202 then calculates the parameter about adhesion between each individual cell 101 and the transparent member 102a, using the image obtained by applying the contour regions of the individual cells 101 determined on the quantitative phase image, to the reflection interference image (which will be referred to hereinafter as "composite image") (step S206, corresponding to "analysis step" in the scope of claims). The processing in the present embodiment is different from the processing in the first embodiment in that, while the analysis unit 202 in the first embodiment defines the measurement region as a region where the cells 101 adhere from the entire reflection interference image, the analysis unit 202 in the present embodiment defines the measurement region as a region of each individual cell.

In the present embodiment, the analysis unit calculates a "change rate of average luminosity" as a parameter to evaluate the change of membrane potential of each individual cell 101 (corresponding to "parameter about adhesion" in the scope of claims). The analysis unit 202 measures the average luminosity of the measurement region as the region of each individual cell as describe above.

When receiving composite images sequentially output from the image alignment unit 211, the analysis unit 202 calculates the average luminosity I(t) of each measurement region in the composite images and calculates a change rate dI relative to the average luminosity of each measurement region acquired in advance before dispensation of a chemical (which will be referred to hereinafter as average luminosity I(base) as a base"). The average luminosity as a base to be used may be, for example, an average luminosity obtained from composite images of individual measurement regions acquired before chemical dispensation, or a default luminosity stored in advance as a default value for each type of cell. Such an average luminosity as a base is stored in the storage unit 203 and the analysis unit 202 retrieves the average luminosity as a base timely from the storage unit 203 and calculates the change rate dI. The change rate dI is calculated by the formula below.

Change rate $dI(t)=\{I(t)-I(\text{base})\}/I(\text{base})$

I(t)=average luminosity of reflection interference (value after correction for background)

I(base)=average of I(t) before chemical dispensation

The analysis unit 202 detects a change of membrane potential of the cells 101 for each measurement region on the basis of the change rate dI calculated by the above formula. Namely, when a predetermined change rate dI is calculated in each individual measurement region, the analysis unit 202 makes such a valuation that there is some change detected in membrane potential in the individual cell 101. The analysis unit 202 may output a graph of a plot along time axis of the change rate dI calculated by the above formula, e.g., graphs as shown in (A) of FIGS. 8 and (B) of FIG. 8. It may also output a graph of a plot of change rate dI (%) to the adhesion area before dispensation of a chemical, as a graph indicating a change of membrane potential of the cells 101. In output of the above graph, it is preferable to output the graph for each of the individual measurement regions or for each of the individual cells.

The membrane potential change detection device 41 of the present embodiment is based on the correlation such that when depolarized, the cells 101 depart from the transparent member 102a to make the reflection interference image brighter and when hyperpolarized, the cells 101 approach the transparent member to make the reflection image darker. Therefore, the device is able to detect the depolarization of each individual cell 101 in membrane potential by the change in the positive direction of the change rate dI and to detect the hyperpolarization of membrane potential of each individual cell 101 by the change in the negative direction of the change rate dI. The device is also able to determine a peak within a certain period after dispensation of the chemical (a maximum in the case of depolarization or a minimum in the case of hyperpolarization) and to make a determination on the concentration of the chemical dispensed to each individual cell 101 from the magnitude of the numerical value.

Operation and Effects of Second Embodiment

The membrane potential change detection device 41 of the second embodiment is provided with the quantitative phase measurement light source 121, the reflection interference measurement light source 106, the reflection interference detection camera 110, the quantitative phase detection camera 125, and the analysis unit 202, whereby the device is able to acquire the information about adhesion of the cells 101 and the information about the area and optical thickness of the cells 101, thereby increasing variations of the parameter about adhesion between the cells 101 and the transparent member 102a. Since the segmentation of the cells 101 is executed by automated processing, it is easy to acquire data on each individual cell 101. When the cells response quick after chemical dispensation and the measurement is desired to be performed at intervals as short as possible, it is effective to adopt the configuration wherein the reflection interference image and the quantitative phase image are acquired simultaneously as in the membrane potential change detection device 41 of the present embodiment.

Modification Example of Second Embodiment

The second embodiment was described using the example in which the contours of the cells acquired from the quantitative phase image were copied to the reflection interference image (segmentation), but the present invention is not limited to this example. For example, the change of membrane potential of the cells 101 can also be detected without passage through the segmentation step. Namely, an entire region indicating the existence of cells 101 obtained by a certain threshold from the quantitative phase image may be defined as the measurement region and the change of membrane potential of cells 101 may be detected using an average luminosity in this measurement region. The calculation of the change rate dI for the average luminosity of the measurement region is the same as that described above and thus the description thereof is omitted herein.

Third Embodiment

The third embodiment of the present invention will be described. In the third embodiment, detailed description will be given for the configuration different from the first embodiment and the same configuration as in the first embodiment will be denoted by the same reference signs, without redundant description.

(Overall Configuration of Membrane Potential Change Detection Device 61)

Figure 19:
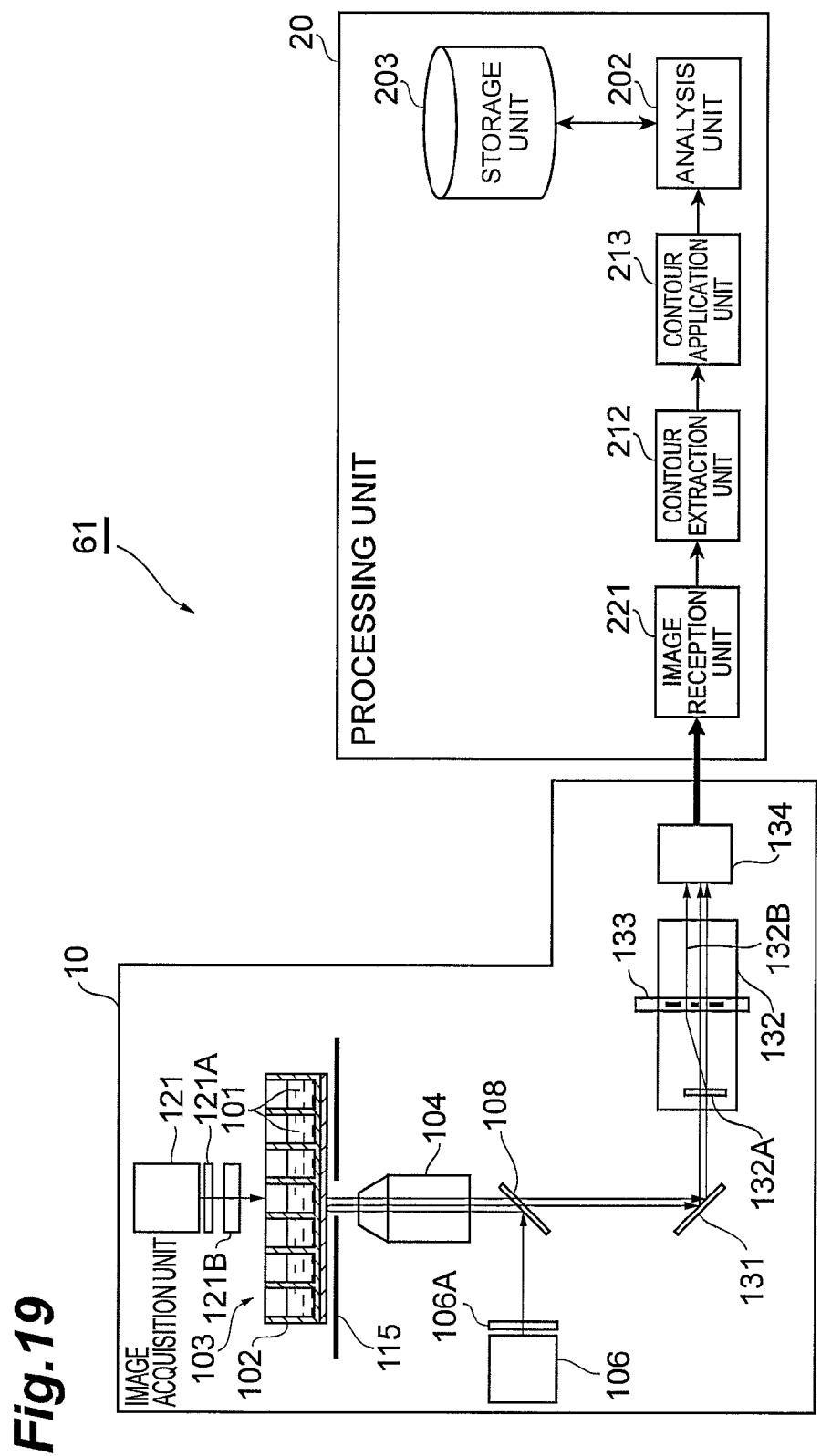
FIG. 19 is a schematic diagram showing an overall configuration of a membrane potential change detection device according to the third embodiment.

First, an overall configuration of a membrane potential change detection device 61 according to an embodiment of the present invention will be described with reference to FIG. 19. FIG. 19 is a schematic diagram showing the overall configuration of the membrane potential change detection device 61. As shown in FIG. 19, the membrane potential change detection device 61 is composed of the image acquisition unit 10 and the processing unit 20.

The image acquisition unit 10 is provided with the holder 103 (corresponding to "holding means" in the scope of claims), the objective lens 104, the quantitative phase measurement light source 121, a quantitative phase shutter 121A (corresponding to "quantitative phase light quantity adjustment means" in the scope of claims), the illumination stop unit 121B, the reflection interference measurement light source 106, a reflection interference shutter 106A (corresponding to "reflection interference light quantity adjustment means" in the scope of claims), the half mirror 108 as a reflection interference illumination optical system, a total reflection mirror 131, a diffractive interference optical system 132, a reference light cutting device 133, and a camera 134 (corresponding to "reflection interference imaging means" in the scope of claims).

The processing unit 20 is provided with an image reception unit 221, the contour extraction unit 212 (corresponding to "contour extraction means" in the scope of claims), the contour application unit 213 (corresponding to "contour application means" in the scope of claims), the analysis unit 202, and the storage unit 203. The image reception unit 221 is a part that receives the reflection interference image and the quantitative phase image generated by imaging of the camera 134. The contour extraction unit 212 is a part that extracts contours as ranges of cells 101, based on the quantitative phase image. The contour application unit 213 is a part that applies the contours extracted by the contour extraction unit 212, to the reflection interference image, to generate a reflection interference image after contour application. The analysis unit 202 is a part that calculates a parameter of each cell 101 about adhesion between the cell 101 and the transparent member 102a, based on the reflection interference image after contour application, and detects a change of membrane potential of each cell 101 on the basis of a change of the parameter. FIG. 2 is a hardware configuration diagram of the processing unit 20 provided with the functional constituent elements as described above. Since the hardware configuration is the same as that in the membrane potential change detection device 1 of the first embodiment, the description thereof is omitted herein.

Figure 24:
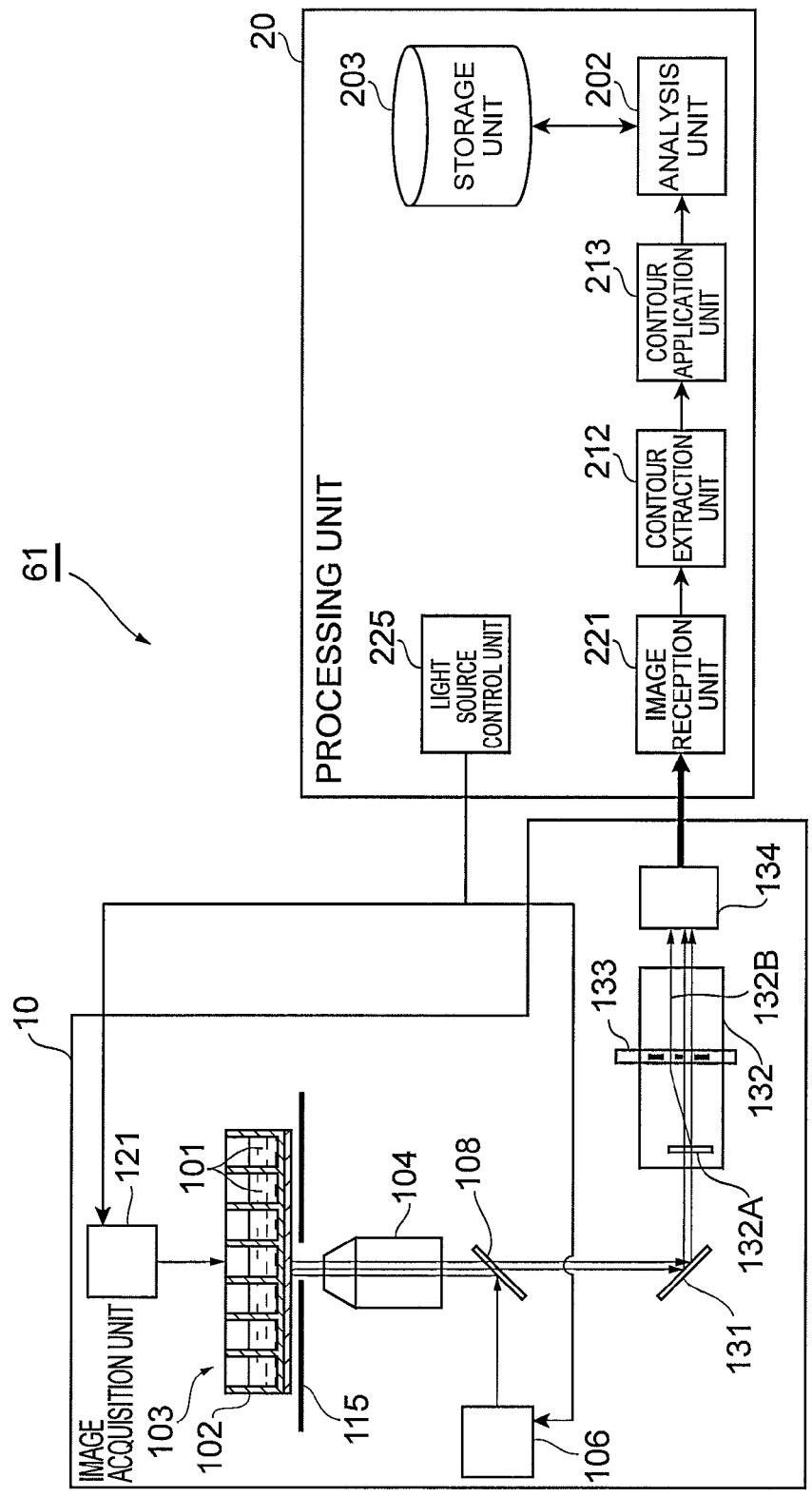
FIG. 24 is a schematic diagram showing an overall configuration of a membrane potential change detection device according to a modification example of the third embodiment.

Next, the image acquisition unit 10 will be described in detail with reference to FIG. 19. The reflection interference shutter 106A adjusts the light quantity of the light emitted from the reflection interference measurement light source 106 such as a halogen lamp or a xenon lamp. The quantitative phase shutter 121A adjusts the light quantity of the light emitted from the quantitative phase measurement light source 121 such as a halogen lamp or a xenon lamp. When the light sources used are those with radiation sensitivity over a wide wavelength range such as halogen lamps or xenon lamps, light in the near infrared region from 700 nm to 2500 nm can be used as illumination light, which can reduce toxicity to the cells 101. When the light sources used are bulb light sources such as halogen lamps or xenon lamps, the light sources had better be kept on without on/off operation of the light sources per se during measurement, with consideration to stability of light quantity, wavelength, and so on. For this, the reflection interference shutter 106A and the quantitative phase shutter 121A are needed. However, when the light sources used are semiconductor light sources such as LEDs (light emitting diodes), semiconductor lasers (laser diodes), or SLDs (super luminescent diodes), switching between reflection interference measurement and quantitative phase measurement may be made by on/off of the light sources themselves. In this case, as shown in FIG. 24, the device is provided with a light source control unit 225 that controls switching of on/off of the reflection interference measurement light source 106 to adjust the light quantity of the light emitted from the reflection interference measurement light source 106 and that controls switching of on/off of the quantitative phase measurement light source 121 to adjust the light quantity of the light emitted from the quantitative phase measurement light source 121. Then, the reflection interference shutter 106A, the quantitative phase shutter 121A, and the illumination stop unit 121B are omitted from the image acquisition unit 10 in the embodiment shown in FIG. 19.

The camera 134 images the reflected light from the cells 101, of the light emitted from the reflection interference measurement light source 106, to generate the reflection interference image and images the transmitted light through the cells 101, of the illumination light emitted from the quantitative phase measurement light source 121 and passing through the illumination stop unit 121B such as a pinhole or an aperture so as to turn into a point light source, to generate the quantitative phase image. During generation of the reflection interference image, as described below, the quantitative phase shutter 121A blocks the light from the quantitative phase measurement light source 121 and then the camera 134 images the reflected light. During generation of the quantitative phase image, the reflection interference shutter 106A blocks the light from the reflection interference measurement light source 106 and then the camera 134 images the transmitted light. As described above, the camera 134 functions as one camera common to the reflection interference measurement and the quantitative phase measurement, which performs the two measurements in a mutually exclusive manner in terms of time.

For generation of the quantitative phase image, the diffractive interference optical system 132 separates the transmitted light through the cells 101 into object light and reference light and causes interference between the object light and the reference light. The reference light cutting device 133 is disposed on the optical path in which the reference light passes in the diffractive interference optical system 132, and blocks the reference light during the generation of the reflection interference image.

The quantitative phase measurement will be described. The illumination light emitted from the quantitative phase measurement light source 121 disposed above the vessel 102 housing the cells 101, travels through the vessel 102 housing the cells 101, to be condensed by the objective lens 104. Then the illumination light travels via the half mirror 108 and then via the total reflection mirror 131 to form an interference image between the object light and the reference light in the diffractive interference optical system 132 for phase measurement, and the interference fringe image is taken by the camera 134.

The reflection interference measurement will be described. The illumination light emitted from the reflection interference measurement light source 106 is reflected by the half mirror 108, passes through the objective lens 104, and is then incident into the vessel 102 housing the cells 101 as a measurement target, from the bottom side thereof. The reflection interference illumination optical system does not always have to be limited to the half mirror, but may be a beam splitter with a reduced reflection ratio, e.g., 5:95 (reflection:transmission) or 20:80 (reflection:transmission), if the intensity of the illumination light is sufficiently high. Furthermore, it is also possible to use a dichroic mirror with the reflectance and transmittance different depending upon wavelengths. The reflected light from the adhesion faces of the cells 101 on the bottom surface of the vessel 102 causes interference according to the adhesion distances of the cells 101, the resultant reflection interference light is condensed again by the objective lens 104, and then the light travels via the half mirror 108 and then via the total reflection mirror 131 to be imaged by the camera 134. The light reflected from the adhesion faces of the cells 101 on the bottom surface of the vessel 102 has different amplitudes of interfering light according to the adhesion distances of the cells 101 and is imaged as a contrast of bright and dark patterns. Since the quantitative phase image and the reflection interference image are acquired through the common objective lens 104, the imaging ranges of the cells 101 are approximately equal between the quantitative phase measurement and the reflection interference measurement.

One of features of the third embodiment is to acquire the quantitative phase image and the reflection interference image alternately with a time difference in between, using one camera 134. For this purpose, the quantitative phase measurement light source 121 and the reflection interference measurement light source 106 need to perform their respective illuminations in a mutually exclusive manner at respective times of emission of the illumination beams. Then there are provided the mechanical shutters 121A, 106A to emit and block light, at the respective irradiation ports of the quantitative phase measurement light source 121 and the reflection interference measurement light source 106. In addition, the reference light cutting device 133 is disposed inside the diffractive interference optical system 132 for creating the quantitative phase image.

The diffractive interference optical system 132 is an optical system for creating the quantitative phase image and functions to separate and extract the object light and the reference light through a diffractive element 132A from the transmitted illumination image under illumination by the quantitative phase measurement light source 121, and to make the object light and the reference light interfere with each other. Since the quantitative phase image and the reflection interference image pass through the same diffractive interference optical system 132, a device for cutting the reference light separated through the diffractive element 132A is needed to extract the reflection interference image, and the present embodiment is provided with the reference light cutting device 133.

Figure 20:
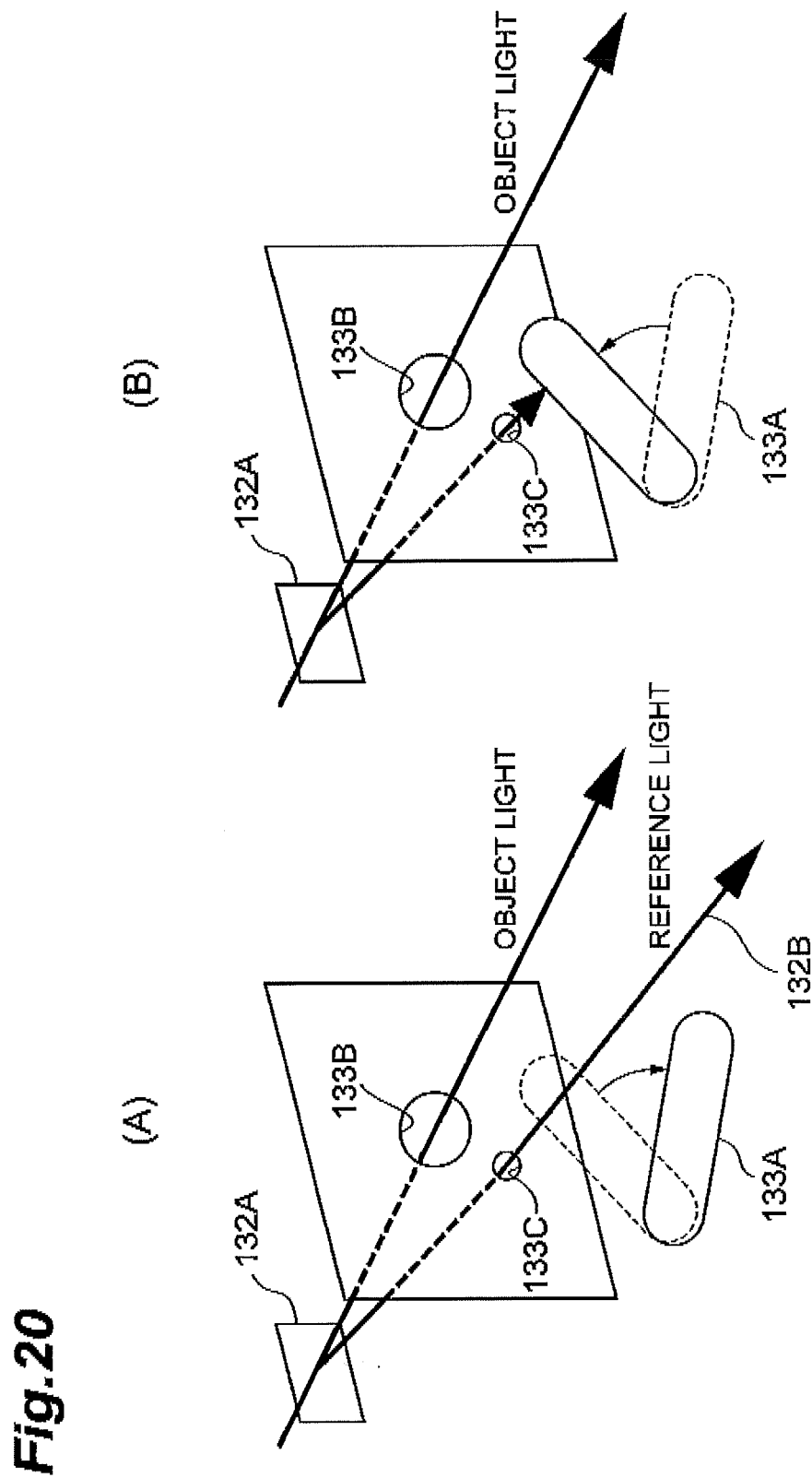
FIG. 20 is a drawing showing a reference light shutter functioning as a reference light cutting device.

The reference light cutting device 133 can be constructed, for example, as a mechanical shutter disposed on the optical path 132B on the reference light side. FIG. 20 is a drawing showing a reference light shutter 133A functioning as the reference light cutting device 133. (A) in FIG. 20 shows motion of the reference light shutter 133A in an imaging operation of the quantitative phase image. The imaging operation of the quantitative phase image necessitates both of the object light through a pinhole 133B and the reference light through a pinhole 133C, after separated by the diffractive element 132A, and therefore the reference light shutter 133A does not block the pinhole 133C, so as to allow the object light and the reference light to pass through the respective pinholes 133B and 133C and reach the camera 134. On the other hand, (B) in FIG. 20 shows motion of the reference light shutter 133A in an imaging operation of the reflection interference image. The imaging operation of the reflection interference image necessitates the object light through the pinhole 133B, after separated by the diffractive element 132A, but does not necessitate the reference light through the pinhole 133C. For this reason, the reference light shutter 133A blocks the pinhole 133C to block the reference light, and only the object light travels through the pinhole 133B to reach the camera 134.

Figure 21:
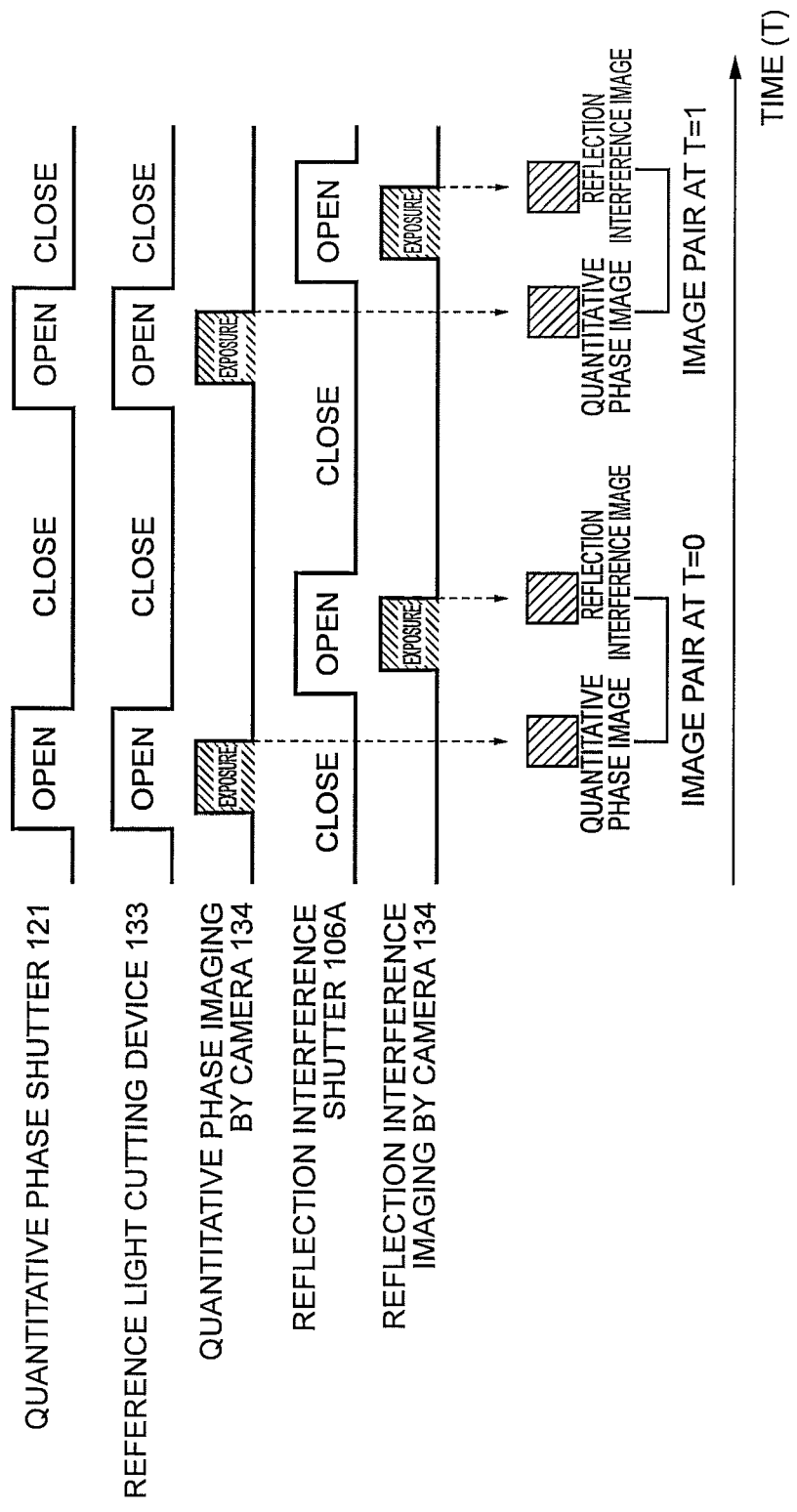
FIG. 21 is a drawing showing a timing chart associated with quantitative phase imaging and reflection interference imaging.

FIG. 21 shows a timing chart associated with the respective operations of the quantitative phase imaging by the quantitative phase shutter 121A, the reference light cutting device 133, and the camera 134, and of the reflection interference shutter 106A and the camera 134. The quantitative phase images and the reflection interference images are acquired by carrying out the illumination and image acquisition in a mutually exclusive manner in time series. Specifically, the quantitative phase shutter 121A is opened and the reflection interference shutter 106A is closed during acquisition of a quantitative phase image. On the contrary, acquisition of a reflection interference image is carried out in such a manner that the reflection interference shutter 106A is opened and the quantitative phase shutter 121A is closed. At the same time, the reference light cutting device 133 disposed on the reference light side out of the object light and the reference light obtained by the diffractive element 132A of the diffractive interference optical system 132 is opened at the timing of acquisition of the quantitative phase image and the camera 134 forms an interference image between the object light and the reference light to obtain the quantitative phase image. On the other hand, since the reference light obtained by the diffractive element 132A is not needed at the timing of acquisition of the reflection interference image, the reference light cutting device 133 disposed on the reference light side is closed and only the object light is focused directly as a reflection interference image, on the camera 134. In this manner the quantitative phase image and the reflection interference image are acquired alternately in terms of time and the two images thus acquired are handled as a pair of images at the same time.

Figure 22:
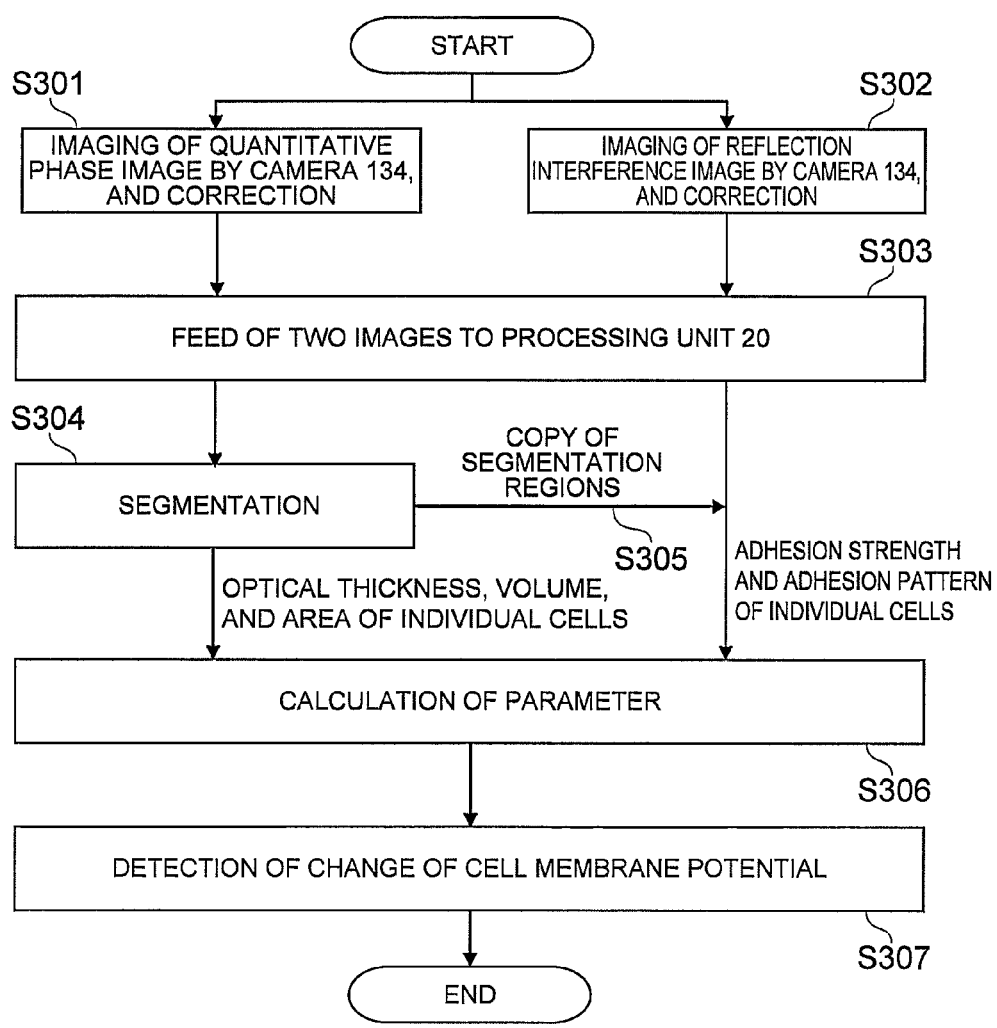
FIG. 22 is a flowchart showing functions and operation of the processing unit according to the third embodiment.

Next, the functions and operation of the processing unit 20 will be described further referring to the flowchart of FIG. 22. First, the camera 134 acquires an interference fringe image between reference light and object light having passed through the cells 101 (step S301, corresponding to "imaging step" in the scope of claims). The quantitative phase image is formed from the interference fringe image by use of a well-known arithmetic method. The quantitative phase image is obtained by making an offset correction for the background region without cells 101 and a shading correction in the field of the background region to make the background part spatially uniform and correct the phase value of the background part to 0, thereby obtaining a two-dimensional map of phases (optical path lengths) of the cells 101.

On the other hand, in parallel with step S301, the camera 134 acquires the reflection interference image of adhesion faces of cells 101 (step S302, corresponding to "imaging step" in the scope of claims). The interfering light has different amplitudes according to distances of the cells 101 adhering to the bottom surface of the vessel 102, from the bottom surface of the vessel 102, and the reflection interference image is taken as a contrast of bright and dark patterns. Correction is made for shading of reflected light in the field of the reflection interference image. In addition, the offset correction for background part is performed in each time unit, in order to prevent temporal variation in value of the background without cells 101. Through these image arithmetic corrections, the quantitative phase image and the reflection interference image can be obtained with little spatial and temporal variations.

The two images (quantitative phase image and reflection interference image) imaged and corrected in step S301 and step S302 are fed to the processing unit 20 (step S303).

Next, a process of extracting the contour regions of the cells 101 (which will also be referred to hereinafter as "segmentation") is performed on the two images fed in step S303 (steps S304 and S305, corresponding to "contour extraction step" and "contour application means" in the scope of claims).

Figure 23:
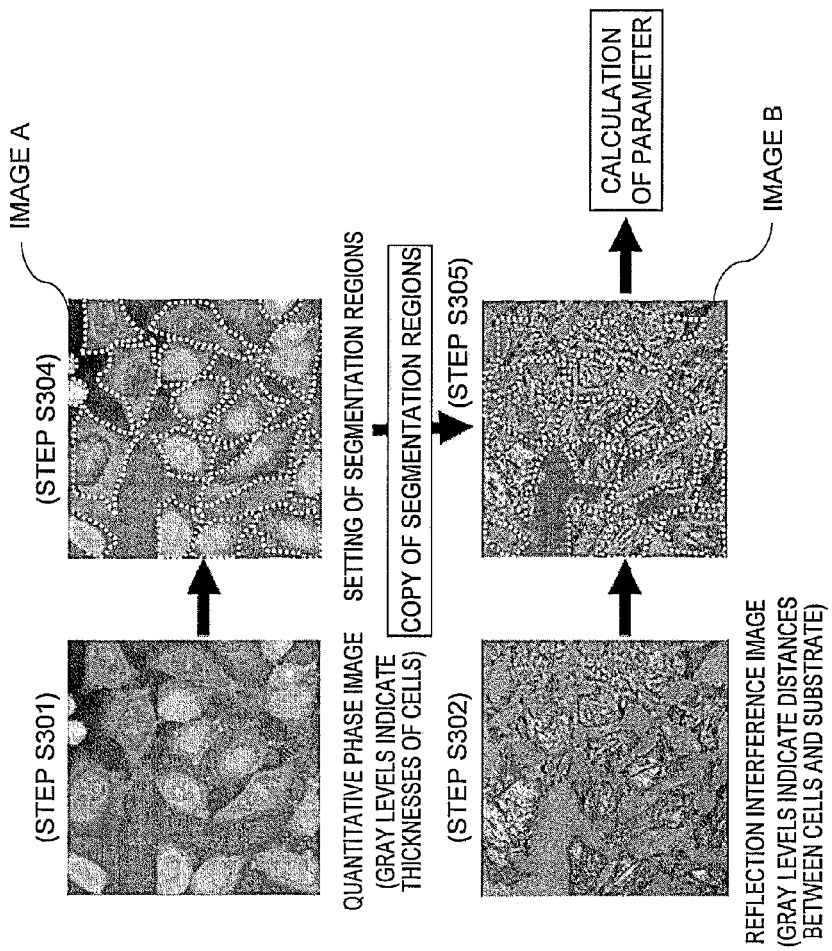
FIG. 23 is a drawing showing an example of the contour extraction process and contour application process according to the third embodiment.

First, as shown in FIG. 23, regions as contours of individual cells 101 are detected from the quantitative phase image out of the quantitative phase image and the reflection interference image after taken at the same observation position and at the same time (step S304, image A in FIG. 23, corresponding to "contour extraction step" in the scope of claims). Namely, in the quantitative phase image, the optical path lengths of light passing through the cells 101 become longer than those of light passing through the solution as the background without the cells 101 therein, because the refractive index of the cells 101 is larger than that of the solution. For this reason, phase values of pixels in the regions where the cells 101 exist become larger than those in the background. Therefore, when an appropriate threshold or spatial filtering process is applied, the cells 101 can be separated from the background automatically without the aid of human hand. Then the contours corresponding to the respective cells 101 can be determined and regions of pixel coordinates corresponding to the regions occupied by the respective cells 101 can be determined.

Next, the pixel coordinates of the contour regions of the individual cells 101 obtained in step S304 are adapted to the reflection interference image aligned in spatial coordinates, i.e., the segmentation regions obtained in step S304 are copied onto the reflection interference image, whereby the contour regions of the individual cells 101 determined on the quantitative phase image are applied to the reflection interference image (step S305, image B in FIG. 23, corresponding to "contour application step" in the scope of claims). By this step, as shown in FIG. 23, the same contour regions can be determined for the two images A, B of the quantitative phase image and the reflection interference image. Furthermore, it is feasible to determine the contour corresponding to each cell and to determine a region of pixel coordinates corresponding to the region occupied by each cell.

The analysis unit 202 calculates a "change rate of average luminosity" of each individual measurement region, using the image obtained by applying the contour regions of the individual cells 101 determined on the quantitative phase image, to the reflection interference image (which will be referred to hereinafter as "composite image"), and detects a change of membrane potential of cell 101 for the individual measurement region on the basis of the change rate dI of average luminosity (step S306, corresponding to "analysis step" in the scope of claims), which is the same as in the second embodiment and the description of which is omitted herein. The present embodiment is also the same in that the analysis unit can determine a peak in a fixed period after dispensation of a chemical to individual cells (a maximum in the case of depolarization or a minimum in the case of hyperpolarization) and then make a determination on a chemical concentration from the magnitude of the numerical value thereof.

Operation and Effects of Third Embodiment

The membrane potential change detection device 61 according to the third embodiment is provided with the quantitative phase measurement light source 121, the quantitative phase shutter 121A, the reflection interference measurement light source 106, the reflection interference shutter 106A, and the camera 134, whereby it is able to simultaneously acquire the information about adhesion of cells 101 and the information about the area and optical thickness of cells 101; therefore, it can increase variations of the parameter about adhesion between the cells 101 and the transparent member 102a. Since the segmentation of cells 101 is carried out by the automated processing, it becomes easier to acquire the data on the individual cells 101.

When the membrane potential change detection device 61 of the third embodiment is compared to the membrane potential change detection device 41 of the second embodiment, only one camera functions to acquire the quantitative phase image and the reflection interference image, which can reduce cost and which provides the advantage of no need for alignment of two cameras. The membrane potential change detection device 61 of the third embodiment is useful to use in applications in which a response of cells to dispensation of a chemical is relatively slow and the change can be detected even in a duration of sequential acquisition of the quantitative phase image and the reflection interference image.

LIST OF REFERENCE SIGNS 1, 41, 61 membrane potential change detection device; 10 image acquisition unit; 20 processing unit; 101 cells; 102 vessel; 102a transparent member; 102b mount surface; 102c bottom surface; 102d antireflection coat; 103 holder; 104 objective lens; 106 reflection interference measurement light source; 106A reflection interference shutter; 107 ring slit; 108 half mirror; 110 reflection interference detection camera; 115 XY stage; 117 dispenser; 121 quantitative phase measurement light source; 121A quantitative phase shutter; 121B illumination stop unit; 122 dichroic mirror; 123, 131 total reflection mirror; 124 diffractive interference optical system; 125 quantitative phase detection camera; 132 diffractive interference optical system; 132A diffractive element; 133 reference light cutting device; 133A reference light shutter; 133B, 133C pinholes; 134 camera; 201, 221 image reception unit; 202 analysis unit; 203 storage unit; 211 image alignment unit; 212 contour extraction unit; 213 contour application unit; 225 light source control unit.

INDUSTRIAL APPLICABILITY

The present invention provides the membrane potential change detection device and the membrane potential change detection method capable of detecting the change of cell membrane potential by the non-invasive method without labeling.

The invention claimed is:

1. A system for detecting a change of membrane potential of a cell mounted on a transparent member, the system comprising:
   a first light source configured to output illumination light for a reflection interference measurement;
   a holder configured to hold the transparent member;
   a detector configured to capture reflected light that is a reflection interference light reflected from an adhesion face of the cell on the transparent member, wherein the reflected light is the illumination light output from the first light source for the reflection interference measurement, thereby generating a reflection interference image; and
   an analyzer configured to calculate a parameter relating to adhesion between the cell and the transparent member based on the reflection interference image and detects a change of membrane potential of the cell based on a change of the parameter.

2. The system according to claim 1, wherein the analyzer detects the change of membrane potential of the cell, based on such a correlation that when depolarized, the cell departs from the transparent member and when hyperpolarized, the cell approaches the transparent member.

3. The system according to claim 1, further comprising:
   an objective lens which condenses the reflected light,
   wherein the objective lens and the transparent member are arranged with an air layer in between.

4. The system according to claim 3, wherein an antireflection coat is laid on a surface of the transparent member opposite to mount surface thereof.

5. The system according to claim 3, further comprising a slit of a ring shape located at a position conjugate with an aperture stop on the first light source side of the objective lens.

6. The system according to claim 1, further comprising:
   a second light source configured to output light for quantitative phase measurement; and
   a detector configured to capture transmitted light that is transmitted through the cell and the transparent member, to generate a quantitative phase image.

7. The system according to claim 6, further comprising:
image alignment unit configured to match a spatial position of the reflection interference image with a spatial position of the quantitative phase image to implement alignment between the two images;
contour extraction unit configured to extract a contour of the cell, based on the quantitative phase image; and
contour application unit configured to apply the contour extracted by the contour extraction unit, to the reflection interference image to generate a reflection interference image after contour application,
wherein the analyzer calculates a parameter of each cell relating to adhesion between the cell and the transparent member, based on the reflection interference image after contour application, and detects a change of membrane potential of each cell based on a change of the parameter.

8. The system according to claim 1, further comprising:
reflection interference light quantity adjustment unit configured to adjust a light quantity of the output light output from the first light source;
a second light source configured to output light for a quantitative phase measurement; and
quantitative phase light quantity adjustment unit configured to adjusts a light quantity of the output light output from the second light source,
wherein the detector captures transmitted light through the cell and the transparent member, of the output light output from the second light source, to generate a quantitative phase image,
wherein during generation of the reflection interference image, the quantitative phase light quantity adjustment unit blocks the output light output from the second light source,
during generation of the quantitative phase image, the reflection interference light quantity adjustment unit blocks the output light output from the first light source,
wherein the reflection interference light quantity adjustment unit is a shutter which adjusts the light quantity of the output light output from the first light source, and
wherein the quantitative phase light quantity adjustment unit is a shutter which adjusts the light quantity of the output light output from the second light source.

9. The system according to claim 8,
wherein the reflection interference light quantity adjustment unit controls switching of on/off of the first light source to adjust the light quantity of the output light output from the first light source, and
wherein the quantitative phase light quantity adjustment unit controls switching of on/off of the second light source to adjust the light quantity of the output light output from the second light source.

10. The system according to claim 8, further comprising:
contour extraction unit configured to extract a contour of the cell, based on the quantitative phase image; and
contour application unit configured to apply the contour extracted by the contour extraction unit, to the reflection interference image to generate a reflection interference image after contour application,
wherein the analyzer calculates a parameter of each cell relating to adhesion between the cell and the transparent member, based on the reflection interference image after contour application, and detects a change of membrane potential of each cell on the basis of a change of the parameter.

11. A method for detecting a change of membrane potential of a cell mounted on a transparent member, the method comprising:
outputting illumination light from a light source for a reflection interference measurement;
capturing reflected light that is a reflection interference light reflected from an adhesion face of the cell on the transparent member, wherein the reflected light is the illumination light output from the light source for the reflection interference measurement, thereby generating a reflection interference image;
calculating a parameter relating to adhesion between the cell and the transparent member based on the reflection interference image; and
detecting a change of membrane potential of the cell based on a change of the parameter.

12. A method for detecting a change of membrane potential of a cell mounted on a transparent member, the method comprising:
outputting illumination light from a first light source for a reflection interference measurement;
capturing reflected light that is a reflection interference light reflected from an adhesion face of the cell on the transparent member, wherein the reflected light is the illumination light output from the first light source for the reflection interference measurement, thereby generating a reflection interference image;
outputting light from a second light source for a quantitative phase measurement;
capturing transmitted light that is transmitted through the cell and the transparent member, to generate a quantitative phase image;
matching a spatial position of the reflection interference image with a spatial position of the quantitative phase image to implement alignment between the two images;
extracting a contour of the cell, based on the quantitative phase image;
applying the extracted contour to the reflection interference image to generate a reflection interference image after contour application;
calculating a parameter of each cell relating to adhesion between the cell and the transparent member, based on the reflection interference image after contour application; and
detecting a change of membrane potential of each cell based on a change of the parameter.

13. A method for detecting a change of membrane potential of a cell mounted on a transparent member, the method comprising:
outputting illumination light from a first light source for a reflection interference measurement;
capturing reflected light that is a reflection interference light reflected from an adhesion face of the cell on the transparent member, wherein the reflected light is the illumination light output from the first light source for the reflection interference measurement, thereby generating a reflection interference image;
outputting light from a second light source for a quantitative phase measurement;
capturing transmitted light that is transmitted through the cell and the transparent member, to generate a quantitative phase image;
extracting a contour of the cell, based on the quantitative phase image;

applying the extracted contour to the reflection interference image to generate a reflection interference image after contour application;

calculating a parameter of each cell relating to adhesion between the cell and the transparent member, based on the reflection interference image after contour application; and detecting a change of membrane potential of each cell based on a change of the parameter, wherein during generation of the reflection interference image, blocking the light from the second light source, and wherein during generation of the quantitative phase image, blocking the light from the first light source.

* * * * *